(12) United States Patent
Mirzaei et al.

(10) Patent No.: US 8,884,214 B2
(45) Date of Patent: *Nov. 11, 2014

(54) METHODS OF USING HALOGENATED PEPTIDES AS INTERNAL STANDARDS FOR LIQUID CHROMATOGRAPHY-MASS SPECTROMETRY

(71) Applicant: Institute for Systems Biology, Seattle, WA (US)

(72) Inventors: Hamid Mirzaei, Seattle, WA (US); Rudolf Aebersold, Zurich (CH)

(73) Assignee: Institute for Systems Biology, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/705,069

(22) Filed: Dec. 4, 2012

(65) Prior Publication Data

US 2013/0193317 A1    Aug. 1, 2013

Related U.S. Application Data

(62) Division of application No. 12/707,137, filed on Feb. 17, 2010, now Pat. No. 8,324,347.

(60) Provisional application No. 61/154,984, filed on Feb. 24, 2009.

(51) Int. Cl.

| | |
|---|---|
| *G01D 18/00* | (2006.01) |
| *A61K 38/04* | (2006.01) |
| *C07K 5/00* | (2006.01) |
| *C07K 7/00* | (2006.01) |
| *C07K 16/00* | (2006.01) |
| *C07K 17/00* | (2006.01) |
| *H01J 49/00* | (2006.01) |
| *C07K 7/08* | (2006.01) |
| *G01N 33/68* | (2006.01) |
| *C07K 7/06* | (2006.01) |
| *C07K 5/107* | (2006.01) |

(52) U.S. Cl.
CPC ......... *H01J 49/0009* (2013.01); *H01J 49/0036* (2013.01); *C07K 7/08* (2013.01); *G01N 33/6848* (2013.01); *C07K 7/06* (2013.01); *G01N 2496/00* (2013.01); *C07K 5/1016* (2013.01)
USPC ........ 250/252.1; 530/326; 530/327; 530/328; 530/329; 530/330

(58) Field of Classification Search
CPC .......... C07K 5/1016; C07K 7/06; C07K 7/08; G01N 2496/00; G01N 33/6848; H01J 49/0009; H01J 49/0036
See application file for complete search history.

(56) References Cited

U.S. PATENT DOCUMENTS

| | | | |
|---|---|---|---|
| 4,211,693 A | 7/1980 | Rivier et al. | |
| 6,629,040 B1 * | 9/2003 | Goodlett et al. | ................. 702/23 |
| 2005/0282731 A1 * | 12/2005 | Bauer et al. | ....................... 514/2 |
| 2006/0263886 A1 * | 11/2006 | Peters et al. | .................... 436/56 |

FOREIGN PATENT DOCUMENTS

| | | |
|---|---|---|
| EP | 1 923 397 | 5/2008 |
| GB | 2 171 103 | 8/1986 |

OTHER PUBLICATIONS

Ferenc et al. Capillary electrophoresis tandem mass spectrometry of bromine-containing charged derivatives of peptides. Journal of Chromatography A, 2007, vol. 1159, pp. 119-124.*
Brittain et al. Enrichment and analysis of peptide subsets using fluorous affinity tags and mass spectrometry. Nature Biotechnology, 2005, vol. 23, No. 4, pp. 463-468.*
Sela et al. Different roles of D-amino acids in immune phenomena. FASEB, 1997, vol. 11, pp. 449-456.*
Niwa et al. Measurement of the novel decapeptide cetrorelix in human plasma and urine by liquid chromatography-electrospray ionization mass spectrometry. Journal of Chromatography B, 1999. vol. 729, pp. 245-253.*
Poethko et al. Two-Step Methodology for High-Yield Routine Radiohalogenation of Peptides: 18F-Labeled RGD and Octreotide Analogs. The Journal of Nuclear Medicine, 2004, vol. 45, No. 5, pp. 892-902.*
Stokvis et al. Stable isotopically labeled internal standards in quantitative bioanalysis using liquid chromatography / mass spectrometry: necessity or not? Rapid Communications in Mass Spectrometry, 2005. vol. 19, pp. 401-407.*
Sysi-Aho et al. Normalization method for metabolomics data using optimal selection of multiple internal standards. BMC Bioinformatics. Mar. 15, 2007, vol. 8, No. 93, pp. 1-17 (as printed).*
Shore et al. Mass Spectrometric Quantification of Polychlorinated Biphenyl Congeners Using Multiple Carbon-13 Internal Standards. Biomed & Environmental Mass Spectrometry, 1986, vol. 13, pp. 15-19.*
Lin et al. Effectivenes of Multiple Internal Standards: Deuterated Analogues of Methylenedioxymethamphetamine, Methylenedioxyamphetamine, Methamphetamine and Amphetamine. Journal of Analytical Toxicology, 2004, vol. 28, pp. 650-654.*
Gerber et al. Absolute quantification of proteins and phosphoproteins from cell lysates by tandem MS. PNAS, 2003. vol. 100, No. 12, pp. 6940-6945.*
Fenselau. A review of quantitative methods for proteomics studies. Journal of Chromatography B, 2007, 855, pp. 14-20.*
Balough, M., "Debating Resolution and Mass Accuracy in Mass Spectrometry," Spectroscopy (2004) 19(10):34-38.
Brusniak et al., "Corra: Computational Framework and Tools for LC-MS Discovery and Targeted Mass Spectrometry-Based Proteomics," BMC Bioinformatics (2008) 9:542.

(Continued)

*Primary Examiner* — Marcela M Cordero Garcia
(74) *Attorney, Agent, or Firm* — Morrison & Foerster LLP

(57) ABSTRACT

Methods of using halogenated peptides as internal standards for liquid chromatography-mass spectrometry, and novel halogenated peptides useful for the same, are disclosed. In particular, methods of using halogenated peptides as internal standards in proteomic analyzes, as well as methods of using halogenated peptides to conduct quality control assessments of and/or to calibrate liquid chromatography-mass spectrometry systems are disclosed.

28 Claims, 10 Drawing Sheets

(56) References Cited

OTHER PUBLICATIONS

Eng et al., "An Approach to Correlate Tandem Mass Spectral Data of Peptides with Amino Acid Sequences in a Protein Database," Journal of American Society for Mass Spectrometry (1994) 5:976-989.

Keller et al., "Empirical Statistical Model to Estimate the Accuracy of Peptide Identifications Made by MS/MS and Database Search," Analytical Chemistry (2002) 74(20):5383-5392.

Lam et al., "Development and Validation of a Spectral Library Searching Method for Peptide Identification from MS/MS," Proteomics (2007) 7(5):655-667.

Lange et al., "Targeted Quantitative Analysis of *Streptococcus pyogenes* Virulence Factors by Multiple Reaction Monitoring," Molecular & Cellular Proteomics (2008) 7(8):1489-1500.

Mirzaei et al., "Enhancing Electrospray Ionization Efficiency of Peptides by Derivatization," Analytical Chemistry (2006) 78(12):4175-4183.

Mirzaei et al., "Halogenated Peptides as Internal Standards (H-PINS)", Molecular and Cellular Proteomics (2009) 8:1934-1946.

Mueller et al., "*SuperHirn*—A Novel Tool for High Resolution LC-MS-Based Peptide/Protein Profiling," Proteomics (2007) 7:3470-3480.

Old et al., "Comparison of Label-Free Methods for Quantifying Human Proteins by Shotgun Proteomics," Molecular & Cellular Proteomics (2005) 4:1487-1502.

Pedrioli et al., "A Common Open Representation of Mass Spectrometry Data and Its Application to Proteomics Research," Nature Biotechnology (2004) 22(11):1459-1466.

Stahl-Zeng et al., "High Sensitivity Detection of Plasma Proteins by Multiple Reaction Monitoring of *N*-Glycosites," Molecular & Cellular Proteomics (2007) 6:1809-1817.

Zhou et al., "Isolation of N-Linked Glycopeptides from Plasma," Analytical Chemistry (2007) 79(15):5826-5837.

\* cited by examiner

METHODS OF USING HALOGENATED PEPTIDES AS INTERNAL STANDARDS FOR LIQUID CHROMATOGRAPHY-MASS SPECTROMETRY

CROSS-REFERENCE TO RELATED APPLICATIONS

This application is a divisional of U.S. patent application Ser. No. 12/707,137, filed 17 Feb. 2010, now issued as U.S. Pat. No. 8,324,347, which claims priority to U.S. Provisional Application No. 61/154,984, filed 24 Feb. 2009. The contents of the above patent applications are incorporated by reference herein in their entirety.

STATEMENT OF GOVERNMENT INTEREST

This invention was made with government support under Contract No. N01-HV-8179, awarded by the National Heart, Lung, and Blood Institute Seattle Proteome Center. The government has certain rights in this invention.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 655652003410SeqList.txt, date recorded: Mar. 15, 2013 size: 4,200 bytes).

BACKGROUND OF THE INVENTION

1. Field of the Invention

The present invention is directed to methods of using halogenated peptides as internal standards for liquid chromatography-mass spectrometry and novel halogenated peptides useful for the same.

2. Description of the Related Art

As proteomics and systems biology converge, the need for the generation of high quality, large scale quantitative proteomic datasets has grown, and so-called label-free quantification has emerged as a very useful platform for their generation. Label-free quantitative experiments are usually designed to detect differentially abundant features in biologically relevant samples by comparing mass versus retention time feature maps generated by liquid chromatography mass spectrometry (LC/MS). Even though label-free proteomic experiments are time and cost effective, they require high levels of reproducibility at every step of the process. Too much variation resulting from sample preparation, liquid chromatography (LC) performance (e.g., injection, gradient delivery, flow rate), and MS performance (e.g., ionization efficiency, mass accuracy, detector performance) can lead to an increase in the false discovery rate (FDR) of detected peptides. Thus it is crucial to minimize such variation in order to adequately control the quality of the data. In addition, label-free experiments are often followed by directed MS/MS analyses, in which selected peptides are specifically targeted for identification, a procedure that also requires high system reproducibility. The total variation in the acquired data is the result of accumulating variation at each step. This variation, regardless of its source, be it from sample handling, injection irreproducibility, change in analyte volume, matrix and co-eluter interference (both suppression and enhancement), system instability, or finally variations in the ion source performance, can be accounted for if an appropriate internal standard system is used.

A more recent development in the field of quantitative proteomics is multi-reaction monitoring (MRM), also referred to as selected reaction monitoring (SRM). This MS-based technology is aimed at fast, sensitive and reproducible screening of large sets of known targets and is ideal for building biological assays in which the presence and quantity of specific analytes is being determined in multiple samples. Certain inputs, such as transitional values (m/z values for the precursor ion and its fragment ions), collision energies and chromatographic retention time are required to build a validated SRM/MRM assay. These values are either extracted from MS/MS data acquired from biological samples with the same type of instrument used for the SRM/MRM analyses, or from a set of peptide standards. To maximize the number of S/MRM measurements in one LC/MS/MS run, the use of elution time constraints has proven highly beneficial. Internal standards can therefore play an integral role in building S/MRM assays, if used to synchronize input values such as retention times between instruments or to monitor the retention time consistency in sequences of scheduled S/MRM experiments.

Internal standards are usually designed to best fit the analytical system for which they are being used. Since the currency of quantitative proteomics is ionized peptide ions, peptides thus represent the best candidates for internal standards for proteomic measurements. However, the use of peptides as internal standards can be challenging when trying to confidently detect the internal standard peptides in ion chromatograms acquired by mass spectral analysis of biological fluids, or other samples of similar complexity, where densely packed features cover the entire mass and time range. In addition, there is always a chance that a peptide with the same elemental composition as the internal standard might exist in the analyte, and thus completely throw off the calibration curve. The same argument is valid for heavy isotope labeled peptides since in many quantitative applications, the analytical matrix is made of heavy isotope labeled peptides. Hence, for a peptide to be useful as an internal standard in proteomic studies, it should have unique properties that make it easily detectable in a background of biological peptides.

Accordingly, while progress has been made in this field, there remains a need in the art for improved internal standards for liquid chromatography-mass spectrometry. The present invention fulfills these needs and provides further related advantages.

BRIEF SUMMARY OF THE INVENTION

In brief, the present invention is directed to methods of using halogenated peptides as internal standards for liquid chromatography-mass spectrometry and novel halogenated peptides useful for the same. In particular, the present invention provides methods of using halogenated peptides as internal standards in proteomic analyses, as well as methods of using halogenated peptides to conduct quality control assessments of, and/or to calibrate, liquid chromatography-mass spectrometry systems (e.g., for sample preparation and liquid chromatography injection quality control, retention time and mass calibration, and signal intensity normalization and retention time synchronization for selected-reaction monitoring).

In a first embodiment, a halogenated peptide is provided selected from the group consisting of H-D-4-bromo-Phe-Lys(Me)$_3$-Arg-Tyr-Gly-OH (SEQ ID NO:1), H-D-4-bromo-Phe- Lys(Me)₃-Gly-Arg-Tyr-Tyr-OH (SEQ ID NO:2), H-D-4-bromo-Phe-Lys(Me)₃-Arg-Tyr-Gly-Tyr-Val-OH (SEQ ID NO:3), H-D-4-bromo-Phe-Lys(Me)₃-Gly-Arg-Tyr-Tyr-Val-Tyr-OH (SEQ ID NO:4), H-His-p-chloro-Phe-p-chloro-Phe-p-chloro-Phe-Ala-Ala-OH (SEQ ID NO:5), H-4-chloro-Phe-4-chloro-Phe-4-chloro-Phe-Lys-NH₂ (SEQ ID NO:6), H-Ala-p-chloro-Phe-p-chloro-Phe-p-chloro-Phe-Ala-Ala-Ala-Lys-NH₂ (SEQ ID NO:7), H-Ile-Ile-p-chloro-Phe-p-chloro-Phe-p-chloro-Phe-Ala-Ala-Lys-NH₂ (SEQ ID NO:8), H-Ile-Ile-p-chloro-Phe-p-chloro-Phe-p-chloro-Phe-Ile-Ile-Ala-Ala-Ala-Ala-Lys-NH₂ (SEQ ID NO:9), and H-Ile-Ile-Ile-p-chloro-Phe-p-chloro-Phe-p-chloro-Phe-Ile-Ile-Ile-Ala-Ala-Ala-Lys-NH₂ (SEQ ID NO:10).

In a second embodiment, a method for identifying and quantifying a peptide in a sample is provided, the method comprising: (a) adding a plurality of halogenated peptide standards to the sample; (b) analyzing the sample using liquid chromatography-mass spectrometry; (c) identifying the liquid chromatography-mass spectrometry data which correspond to the peptide; (d) identifying the liquid chromatography-mass spectrometry data which correspond to the halogenated peptide standards; and (e) quantifying the amount of the peptide in the sample using the data identified in steps (c) and (d).

In a third embodiment, a method for monitoring performance of a liquid chromatography-mass spectrometry system is provided, the method comprising: (a) adding a plurality of halogenated peptide standards to a sample; (b) analyzing the sample using the liquid chromatography-mass spectrometry system; (c) identifying the liquid chromatography-mass spectrometry data which correspond to the halogenated peptide standards; (d) using the data identified in step (c) to conduct a quality control assessment of the liquid chromatography-mass spectrometry system or to calibrate the liquid chromatography-mass spectrometry system.

In a fourth embodiment, an internal standard kit for use in liquid chromatography-mass spectrometry is provided, wherein the internal standard kit comprises a plurality of halogenated peptide standards.

These and other aspects of the invention will be apparent upon reference to the following detailed description.

DETAILED DESCRIPTION OF THE INVENTION

Figure 1A:
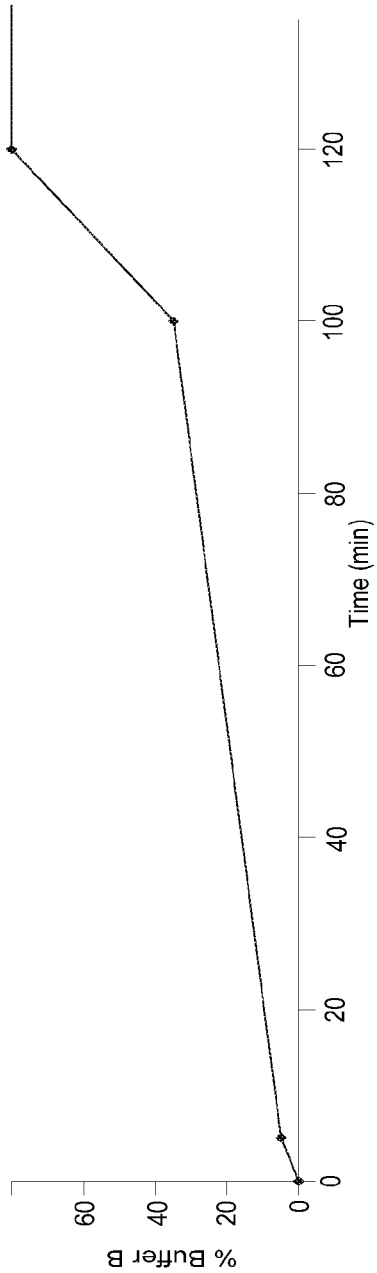
FIGS. 1A-1D show representative LC/MS data: a) gradient used for separation of a glycocapture stock solution spiked with H-PINs (FIG. 1A), b) TIC of a glycocapture stock solution spiked with H-PINs (FIG. 1B), c) extracted ion chromatograms of representative H-PINs (FIG. 1C), and d) mass and isotopic distributions of representative H-PINs (FIG. 1D).
Figure 1B:
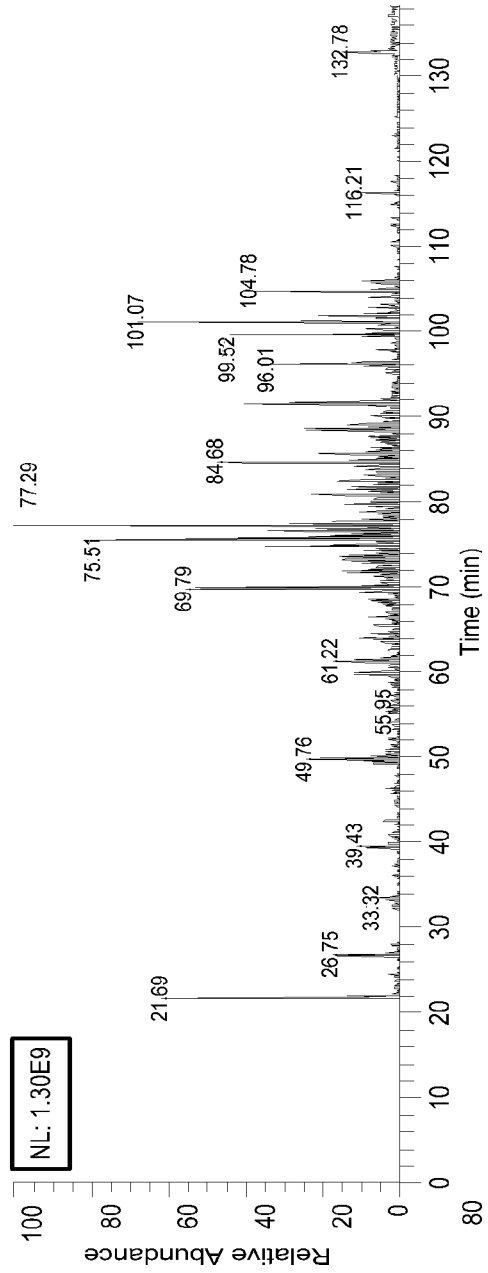
Figure 1C:
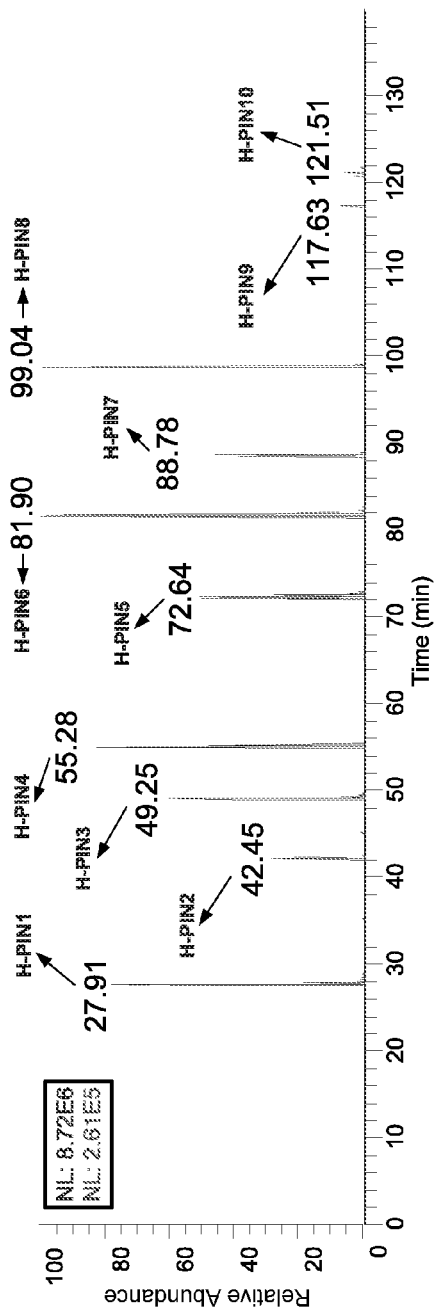
Figure 1D:
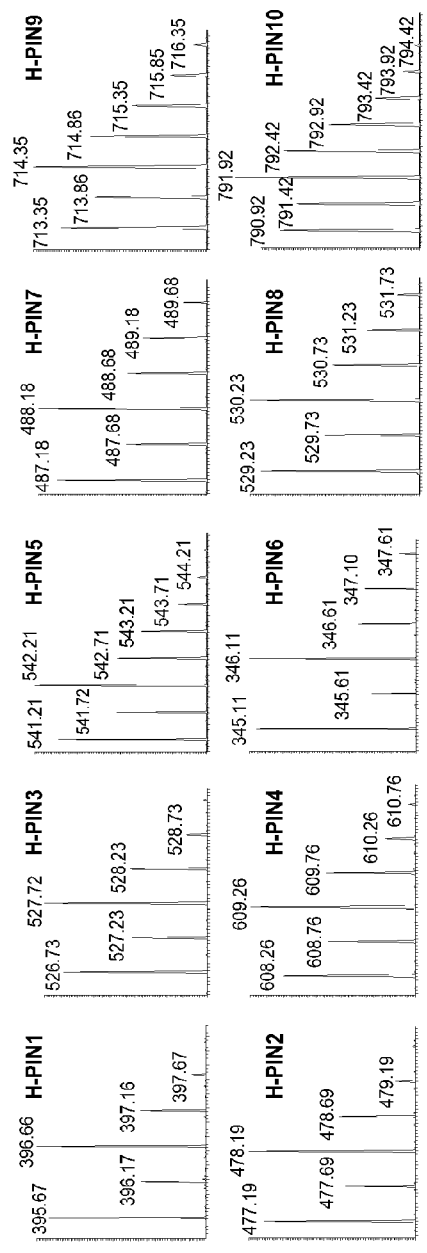

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino acid" or "amino acid residue" refers to any naturally occurring or any non-natural compound containing both an amine and carboxylic acid functional group. The naturally occurring amino acids may be referred to using the three letter code known to those of ordinary skill in the art. For example, as used herein, amino acids and their corresponding three letter codes are as follows: alanine (Ala), arginine (Arg), Asparagine (Asn), aspartic acid (Asp), cysteine (Cys), glutamic acid (Glu), glutamine (Gln), glycine (Gly), histidine (His), isoleucine (Ile), leucine (Leu), Lysine, (Lys), methionine (Met), phenylalanine (Phe), proline (Pro), serine (Ser), threonine (Thr), tryptophan (Trp), tyrosine (Tyr), and valine (Val). In addition, non-natural amino acids may be referred to using similar nomenclature. For example, as used herein, 4-chloro-Phe, 4-bromo-Phe, and Lys(Me)₃ refers to 4-chlorophenylalanine, 4-bromophenylalanine, and trimethyllysine, respectively. An amino acid name or abbreviation may also be preceded by a letter, either D, L, or D/L, which indicates whether the amino acid is in the D, L, or racemic (D/L) configuration. If the D or L configuration is not specified, the amino acid is in the naturally occurring L configuration.

"Amine" refers to a nitrogen containing compound.

"Analyzing" refers to performing any operation or function to obtain data. For example, analyzing a mixture by high performance liquid chromatography-mass spectrometry (LC/MS) refers to subjecting the mixture to LC/MS to obtain the corresponding chromatogram and mass spectrum. Methods for analyzing mixtures and other samples by LC/MS are disclosed herein and are well known in the art.

"Biological sample" refers to biological fluid, cell, tissue, organ, or portion thereof, that includes one or more different molecules such as nucleic acids, polypeptides, or small molecules. A biological sample can be a tissue section obtained by biopsy, or cells that are placed in or adapted to tissue culture. A biological sample can also be a biological fluid specimen such as blood, serum or plasma, cerebrospinal fluid, urine, saliva, seminal plasma, pancreatic juice, breast milk, lung lavage, and the like. A biological sample can additionally be a cell extract from any species, including prokaryotic and eukaryotic cells as well as viruses. A tissue or biological fluid specimen can be further fractionated, if desired, to a fraction containing particular cell types.

"Carboxyl terminus" refers to the end of a peptide containing a free carboxylic acid group. For example, an amino acid located at the carboxyl terminus of a peptide is only bound to one other amino acid, which bond is through the amine group of the carboxyl terminal amino acid.

"Carboxylic acid" refers to the —C(=O)OH group.

"Halo" or "halogen" refers to bromo, chloro, fluoro or iodo.

"Halogenated amino acid" refers to any amino acid comprising at least one halogen atom.

"Halogenated peptide" or "H-PIN" refers to any peptide comprising at least one halogenated amino acid.

"Halogenated peptide standard" refers to a halogenated peptide suitable for use as an internal standard.

The "internal position" of a peptide refers to any position which is neither the N-terminal nor the carboxyl terminal position.

"N-terminus" refers to the end of a peptide containing a free amine group. For example, an amino acid located at the N-terminus of a peptide is only bound to one other amino acid, which bond is through the carboxylic acid group of the N-terminal amino acid.

"Peptide" is used in its conventional meaning, i.e., as a sequence of amino acids. A peptide may be formed when the amine group of a first amino acid bonds with the carboxylic acid group of a second amino acid to form a peptide bond (also known as an amide). The peptides are not limited to a specific length of the product; thus, polypeptides, oligopeptides, and proteins are included within the definition of peptide, and such terms may be used interchangeably herein unless specifically indicated otherwise. A peptide can also be modified by naturally occurring modifications such as post-translational modifications, including phosphorylation, fatty acylation, prenylation, sulfation, hydroxylation, acetylation, addition of carbohydrate, addition of prosthetic groups or cofactors, formation of disulfide bonds, proteolysis, assembly into macromolecular complexes, and the like. A "peptide fragment" is a peptide of two or more amino acids, generally derived from a larger peptide.

As used herein, a peptide sequence may be represented by a series of amino acid three letter codes connected by a hyphen (-). It is understood that the amino acids are listed in order beginning from the N-terminus. An "H" preceding a peptide sequence indicates the free amine at the N-terminus. Similarly, an "OH" following a peptide sequence indicates the free carboxyl group at the C-terminus. An "$NH_2$" following a peptide sequence indicates the carboxyl group at the C-terminus has been replaced with an $NH_2$ group resulting in an amide.

"Stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another. The present invention also includes "diastereomers", which refers to stereoisomers which are not enantiomers.

"Tautomer" refers to a proton shift from one atom of a molecule to another atom of the same molecule. The present invention includes tautomers of any disclosed compound.

As noted above, the present invention provides methods of using halogenated peptides as internal standards for liquid chromatography-mass spectrometry and novel halogenated peptides useful for the same. As discussed previously, the reliability of quantitative proteomics is tightly linked to the reproducibility and stability of the analytical platforms utilized, which are typically multi-component (e.g., sample preparation, multi-step separations, and mass spectrometry) with individual components contributing unequally to the overall system reproducibility. Variations in quantitative accuracy are thus inevitable, and quality control and calibration have become essential for the assessment of the quality of the analyses themselves. Towards this end, the use of the internal standards of the present invention can not only assist in the detection and removal of outlier data acquired by an irreproducible system (quality control), but can also be used for detection of changes in instruments for their subsequent performance and calibration.

With respect to the halogenated peptides of the present invention, for a peptide to be useful as an internal standard, it should produce a distinguishable mass spectral signal. A mass spectral signal for a typical peptide ion includes the mass, isotopic distribution, and intensity. This mass signal by itself is not enough to distinguish a peptide in a complex mixture because a typical peptide matrix contains thousands of features, densely covering the entire mass range. This is complicated by the fact that the isotopic distribution of all natural peptides is quite similar due to their similar elemental composition (carbon, nitrogen, oxygen, and sulfur). However, the unique isotope distribution of the halogenated peptides of the present invention makes their mass spectral detection (by, e.g., manual search and automated peak picking algorithms) easy and unambiguous when spiked into complex peptide mixtures. In this regard, halogens have a different isotopic pattern than most elements (the abundance of the heavy isotope is considerably higher in halogens than in other elements). In addition, halogens have a negative mass defect which shifts the mass of halogenated peptides slightly to the lower values than peptides with the same nominal mass.

In addition, the halogenated peptides of the present invention possess the following additional characteristics which make them suitable for use as internal standards. First, the halogenated peptides have unique isotopic distributions which are spread across the entire LC gradient. In addition, the halogenated peptides include a balance of hydrophilic and hydrophobic amino acids, such that the halogenated peptides elute sequentially over an entire aqueous to organic LC gradient. Furthermore, the halogenated peptides have mass to charge (m/z) values within the commonly scanned mass range (300 to 1800 Da). Although the halogenated peptides ionize well in electrospray ionization (ESI) mode, the halogenated peptides can exhibit features which improve their ionization, such as an amidated C-terminus or inclusion of a $Lys(Me)_3$ moiety.

In certain embodiments, a plurality of halogenated peptide standards are provided wherein each halogenated peptide standard independently comprises from about 2 to about 20 amino acid residues.

In certain embodiments, each halogenated peptide standard independently comprises from 1 to 5 halogenated amino acid residues.

In certain embodiments, each halogenated amino acid residue independently comprises one or more halogen atoms selected from chlorine and bromine.

In certain embodiments, each halogenated amino acid residue is halogenated phenylalanine. For example, in more specific embodiments, each halogenated amino acid residue is independently selected from 4-chlorophenylalanine and 4-bromophenylalanine.

In certain embodiments, at least one of the halogenated peptide standards comprises a halogenated amino acid residue at the N-terminus of the halogenated peptide standard.

In certain embodiments, at least one of the halogenated peptide standards comprises a halogenated amino acid residue at the carboxyl terminus of the halogenated peptide standard.

In certain embodiments, at least one of the halogenated peptide standards comprises one or more halogenated amino acid residues at an internal position of the halogenated peptide standard.

In certain embodiments, each halogenated peptide standard independently comprises amino acid residues selected from D and L amino acid residues.

In certain embodiments, each halogenated peptide standard independently has a mass to charge ratio of about 200 to about 2,000.

In certain embodiments, each halogenated peptide standard independently elutes within the aqueous, organic, or mixed aqueous/organic portion of a high performance liquid chromatography gradient.

In certain embodiments, the plurality of halogenated peptide standards comprise H-D-4-bromo-Phe-Lys(Me)$_3$-Arg-Tyr-Gly-OH (SEQ ID NO:1), H-D-4-bromo-Phe-Lys(Me)$_3$-Gly-Arg-Tyr-Tyr-OH (SEQ ID NO:2), H-D-4-bromo-Phe-Lys(Me)$_3$-Arg-Tyr-Gly-Tyr-Val-OH (SEQ ID NO:3), H-D-4-bromo-Phe-Lys(Me)$_3$-Gly-Arg-Tyr-Tyr-Val-Tyr-OH (SEQ ID NO:4), H-His-p-chloro-Phe-p-chloro-Phe-p-chloro-Phe-Ala-Ala-OH (SEQ ID NO:5), H-4-chloro-Phe-4-chloro-Phe-4-chloro-Phe-Lys-NH$_2$ (SEQ ID NO:6), H-Ala-p-chloro-Phe-p-chloro-Phe-p-chloro-Phe-Ala-Ala-Ala-Lys-NH$_2$ (SEQ ID NO:7), H-Ile-Ile-p-chloro-Phe-p-chloro-Phe-p-chloro-Phe-Ala-Ala-Lys-NH$_2$ (SEQ ID NO:8), H-Ile-Ile-p-chloro-Phe-p-chloro-Phe-p-chloro-Phe-Ile-Ile-Ala-Ala-Ala-Ala-Lys-NH$_2$ (SEQ ID NO:9), and H-Ile-Ile-Ile-p-chloro-Phe-p-chloro-Phe-p-chloro-Phe-Ile-Ile-Ile-Ala-Ala-Ala-Lys-NH$_2$ (SEQ ID NO:10).

The halogenated peptides of the invention can contain one or more asymmetric centers and can thus give rise to enantiomers, diastereomers, and other stereoisomers that can be defined in terms of their absolute (D) or (L) stereochemistry. The present invention is meant to include halogenated peptides comprising only (D) amino acids, only (L) amino acids, or any combination of (D) and (L) amino acids. The halogenated peptides may be present in their optically pure form, racemic form, or in any combination thereof. Optically active (D) and (L) amino acid isomers may be prepared using chiral synthons or chiral reagents, or resolved using conventional techniques, for example, chromatography and fractional crystallization. Alternatively, amino acids may be isolated from natural sources. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). Likewise, all tautomeric forms of the halogenated peptides are also intended to be included within the invention.

As further noted above, also disclosed herein are internal standard kits for use in liquid chromatography-mass spectrometry, wherein the internal standard kit comprises a plurality of the foregoing halogenated peptides.

As further noted above, also disclosed herein are methods of using the foregoing halogenated peptides for liquid-chromatography. In particular, disclosed herein are methods of using halogenated peptides as internal standards in proteomic analyses, as well as methods of using halogenated peptides to conduct quality control assessments of, and/or to calibrate, liquid chromatography-mass spectrometry systems (e.g., for sample preparation and liquid chromatography injection quality control, retention time and mass calibration, and signal intensity normalization and retention time synchronization for selected-reaction monitoring).

In a first embodiment, a method for identifying and quantifying a peptide in a sample is provided, the method comprising: (a) adding a plurality of halogenated peptide standards to the sample; (b) analyzing the sample using liquid chromatography-mass spectrometry; (c) identifying the liquid chromatography-mass spectrometry data which correspond to the peptide; (d) identifying the liquid chromatography-mass spectrometry data which correspond to the halogenated peptide standards; and (e) quantifying the amount of the peptide in the sample using the data identified in steps (c) and (d).

In a second embodiment, a method for monitoring performance of a liquid chromatography-mass spectrometry system is provided, the method comprising: (a) adding a plurality of halogenated peptide standards to a sample; (b) analyzing the sample using the liquid chromatography-mass spectrometry system; (c) identifying the liquid chromatography-mass spectrometry data which correspond to the halogenated peptide standards; (d) using the data identified in step (c) to conduct a quality control assessment of the liquid chromatography-mass spectrometry system or to calibrate the liquid chromatography-mass spectrometry system.

In further embodiments, step (d) of the foregoing method comprises using the data identified in step (c) to: (i) determine the limit of an intensity normalization process used with the liquid chromatography-mass spectrometry system and eliminate liquid chromatography-mass spectrometry data with variations beyond the limit; (ii) determine whether variation in liquid chromatography-mass spectrometry system data of the liquid chromatography-mass spectrometry system is due to sample preparation or performance of the liquid-chromatography-mass spectrometry system; (iii) to recalibrate miscalibrated liquid chromatography-mass spectrometry data; (iv) monitor the performance of a liquid chromatography column of the liquid chromatography-mass spectrometry system; or (v) synchronize the retention times between a first liquid chromatography system and a second liquid chromatography system of the liquid chromatography-mass spectrometry system. Specific embodiments of the foregoing quality control assessments and calibration steps are set forth in the Examples below.

In further embodiments, the sample is a biological sample. For example, in more specific embodiments, the biological sample is a body fluid, secreted proteins, cell surface proteins, plant-derived material, or a microorganism. For example, human plasma.

It is understood that any embodiment of the methods, internal standards kits, uses thereof, and halogenated peptides as set forth above may be independently combined with other embodiments to form embodiments of the invention not specifically set forth above.

The following Reaction Scheme illustrates a method of making halogenated peptides of the present invention. It is understood that one skilled in the art may be able to make these peptides by similar methods or by combining other methods known to one skilled in the art. It is also understood that one skilled in the art would be able to make, in a similar manner as described below, other halogenated peptides not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Advanced Organic Chemistry: Reactions, Mechanisms, and Structure, 5th edition (Wiley, December 2000), which is incorporated herein by reference in its entirety to the extent not inconsistent with the present disclosure) or prepared as described in this disclosure.

(PNGase F) was purchased from Roche® Diagnostics (Indianapolis, Ind., USA). $C_{18}$ PepMap™ 100 reversed-phase $C_{18}$ column (0.075×150 mm) was purchased from Dionex, Inc (Sunnyvale, Calif., USA). Mass Spectrometry Grade Trypsin Gold was purchased from Promega (Madison, Wis., USA). Mass spectra were acquired using an Agilent 1100/LTQ-Orbitrap® mass spectrometer (Thermo-Finnigan, San Jose,

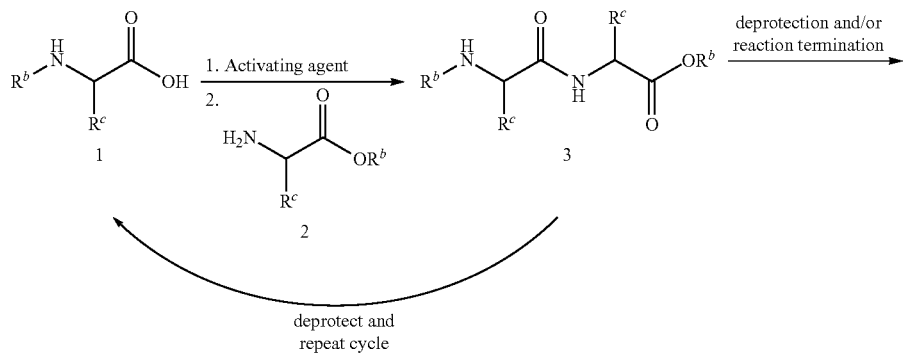

Reaction Scheme 1

Halogenated peptides of the invention can be prepared according to Reaction Scheme 1. Referring to Reaction Scheme 1, $R^b$, at each occurrence, represents a suitable protecting group, a solid support, a peptide, or an amino acid, and $R^c$, at each occurrence, represents any natural or non-natural amino acid side chain. Compound 1 can be purchased or prepared according to methods known to those skilled in the art and reacted with a suitable activating reagent, such as a carbodiimide or a triazole. A suitably protected amino acid 2 can be purchased or prepared according to methods known to those skilled in the art and reacted with the previously activated compound to form peptide 3. Peptide 3 can then be deprotected and/or the reaction cycle can be terminated to obtain the desired halogenated peptide. Alternatively, the reaction cycle may be repeated to increase the chain length of the peptide. One skilled in the art will recognize that similar common methods for automated solid-phase synthesis of both natural and non-natural peptides exist. Suitable protecting groups for synthesizing the halogenated peptides of the invention include tert-butoxycarbonyl (t-Boc), 9H-fluoren-9-ylmethoxycarbonyl (Fmoc), benzyloxycarbonyl, allyloxycarbonyl, and the like. Alternatively, the halogenated peptides of the invention can be expressed in bacteria using methods known to those skilled in the art.

The following examples are provided for purposes of illustration, not limitation.

EXAMPLES

Referring to the examples that follow, representative H-PINs (see Table 2 for a complete list) were purchased as a custom item from BACHEM USA (Torrance, Calif., USA). Male human plasma was purchased from Bioreclamation Inc. (Hicksville, N.Y., USA). Trifluoroacetic acid (TFA), trifluoroethanol (TFE), sodium periodate, tris(2-carboxylethyl) phosphine (TCEP), and iodoacetamide were purchased from Pierce Co. (Rockford, Ill., USA). HPLC-grade acetonitrile (ACN) and HPLC grade water with 0.1% formic acid were purchased from Mallinckrodt (St. Louis, Mo., USA). Affi-Prep® hydrazide resin was purchased from BioRad® laboratories (Hercules, Calif., USA). Protein N-glycosidase F Calif.) with a Tempo 2D-NanoLC/4000QTrap™ (Applied Biosystems (ABI), CA, USA). All spectra were obtained in the positive ion mode.

LC/MS/MS analyses were performed as follows. All samples were separated on a reversed-phase column packed with Magic C18AQ packing materials (5 µm particle size, 100 Å pore size) in 75 µm fritted capillary tubing (New Objectives, Woburn, Mass.), using a Proxeon EASY-nLC™ system (Odense, Denmark) at 250 nL/min. Buffer A was 0.1% formic acid in deionized $H_2O$ (dI $H_2O$) and buffer B was 98% ACN/ 0.1% formic acid in dI $H_2O$. Flow from the column was directed to a LTQ-Orbitrap® workstation (Thermo-Finnigan, San Jose, Calif.) equipped with a nano-ESI source. Peptides were separated using a 95 min linear gradient (from 5% to 35% buffer B) and MS/MS spectra were acquired in positive ion mode at 1500 volts of ionization voltage and 20 units of curtain gas at a sampling rate of one spectrum per second. The top five peptides with charges ranging from 2+ to 4+ were selected for CID, and once they were selected for CID they were excluded from re-selection for 60 sec. SEQUEST was used for all database searches (see Eng, J., et al., *J. Am. Soc. Mass Spectrum* 5, 976-989 (1994), which is incorporated herein by reference in its entirety to the extent not inconsistent with the present disclosure).

The following search parameters were used for peptide identification: the IPI Human.V3.34 database was used; proteolysis was achieved with trypsin; up to 2 miscleavages were allowed. Conversion of asparagine to aspartic acid (which results from the deglycosylation by PNGaseF) and oxidation of methionine were used as variable modifications; alkylation of cysteine by iodoacetamide was used as a fixed modification; the peptide mass tolerance was set at ±1.5 Da; mass tolerance for fragment ions was set at ±3.0 Da, the charge was specified for each peptide; and monoisotopic peaks were used for identification. The PeptideProphet scoring system was used as a measure of identification confidence. The cut-off score was set to allow a 1.7% false discovery rate (see Keller, A., et al., *Anal. Chem.* 74(20):5383-92 (2002), which is incorporated herein by reference in its entirety to the extent not inconsistent with the present disclosure).

LC/MRM analyses were performed as follows. H-PINs and other peptides from the glycocapture stock solution (see Example 1 below) were separated on a LC PACKINGS Pep-Map™ 100 reversed-phase C18 column (0.075×150 mm) using a Tempo 2D nano-LC system from Eksigent (Eksigent Technologies, LLC. Dublin, Calif., USA) at 200 nL/min. Flow from the column was directed to a 4000QTrap® workstation (Applied Biosystems, Framingham, Mass.) equipped with a nano-ESI source. S/MRM spectra were acquired in positive ion mode at 3000 volts of ionization voltage and 30 units of nebulizer gas. The three most intense transitions were selected from the S/MRM spectra for each H-PIN to generate the final list of S/MRM transitions.

Quantifications were done using two different algorithms. Initially all feature extraction and quantifications were done using the Quan Browser functionality of the Xcalibur software. For the automated processing of LC/MS runs with spiked in H-PINs, the open source program SuperHirn was adapted to recognize the isotopic distribution of the H-PINs (see Mueller, L. et al., *Proteomics* 7:3470-3480 (2007), which is incorporated herein by reference in its entirety to the extent not inconsistent with the present disclosure). Following peak picking, the extracted H-PINs were specially labeled and aligned together with all detected MS1 features across the different LC/MS runs into a MasterMap. The modified version of SuperHirn is integrated into the latest Corra software release. All normalizations were done using non linear quantile normalization used in Corra software (see Brusniak, M., et al., "Computational framework and tools for LC-MS discovery and targeted mass spectrometry-based proteomics," *BMC Bioinformatics*, in press (2008), which is incorporated herein by reference in its entirety to the extent not inconsistent with the present disclosure).

Example 1

Extracting Peptides From Human Plasma (Serum Glycocapture)

Glycocapture was performed at the peptide level using the protocol described by Zhou et al. (see Zhou, Y., et al., *Anal. Chem.* 79, 5826-5837 (2007), which is incorporated herein by reference in its entirety to the extent not inconsistent with the present disclosure). Aliquots of 50 µl of male human plasma were first diluted with the same volume of 100 mM ammonium bicarbonate (pH 8.3), and proteins were then denatured by slowly adding trifluoroethanol (TFE) up to 50% (v/v) final concentration. After the cysteine residues were reduced by TCEP (5 mM) and alkylated in iodoacetamide (10 mM) for 0.5 hour each at room temperature, the samples were further diluted ten fold with 100 mM ammonium bicarbonate to a final volume of about 2 mL.

Proteins were then digested with 40 µg of sequence-grade trypsin overnight at 37° C. and cleaned up by $C_{18}$ spin columns (500 mg, Waters, Milford, Mass.). The eluates were then dried down under vacuum in a SpeedVac™ and resuspended in 450 µL of coupling buffer (100 mM sodium acetate, 1 M sodium chloride, pH 4.5). After being oxidized in 10 mM $NaIO_4$ for 1 h at room temperature in the dark, the peptides were cleaned up using $C_{18}$ spin columns. The peptides were eluted with 4 mL of 80% ACN in 0.1% TFA and directly mixed with 50 µL of Affi-Prep® hydrazide resin slurry equilibrated with coupling buffer (pH 4.5). The resulting mixture was shaken overnight at room temperature. Non-specifically bound peptides were then removed by washing the resin sequentially with 3 portions of 1.5 M NaCl, 80% acetonitrile, Milli-Q® water and finally 0.1 M $NH_4HCO_3$. N-glycosylated peptides were finally released from the resin by adding 1 µL of PNGase F and incubating overnight at 37° C. The released peptides were extracted by washing twice with 200 µL of 80% ACN, and further cleaned up using 96 well µElution MCX plates (Waters, Milford, Mass.) before being analyzed on a LCQ Classic ion trap mass spectrometer (Thermo-Finnigan, San Jose, Calif.). The final volume was adjusted to 1600 µL for a 250 µL serum aliquot and used as a stock solution (referred to herein as the "glycocapture stock solution") for all experiments. The glycocapture stock solution was stored at −80° C. until used.

Example 2

Concentration and Intensity Optimization for H-PINS

The ionization efficiency of peptides during ESI is variable and matrix-dependent. Thus, to generate an internal standard mixture with similar signal intensities for each internal standard, the sample load level for each H-PIN was optimized to generate a set of H-PINs with similar signal intensity (see Mirzaei, H., et al., *Anal. Chem.* 78, 4175-83 (2006), which is incorporated herein by reference in its entirety to the extent not inconsistent with the present disclosure). The criteria for adjusting the H-PIN concentrations were as follows: 1) reach a signal with S/N≥100; 2) avoid chromatographic carryover; 3) avoid chromatographic artifacts such as fronting and tailing to help optimal quantification; and 4) avoid interference with data-dependent acquisition (DDA) and peptide identifications.

H-PINs 1-7 (see Table 2 below) were solubilized in 2% ACN, 0.1% TFA and H-PINs 8-10 (see Table 2 below) were solubilized in 80% ACN, 0.1% TFA to a final concentration of 200 µg/mL. An H-PIN cocktail containing an equimolar solution of all ten H-PINs was prepared and used to generate a 1000-fold dilution series to simulate a complex biological sample. 1 µL of the H-PIN cocktail from each dilution (1×, 10×, 100×, 1000×) was spiked into 9 µL of the glycocapture stock solution from Example 1 and analyzed by LC/MS for peak intensity detection using a 95 min linear gradient from 5 to 35% buffer B (98% ACH/0.1% formic acid). Buffer blanks were injected after each sample injection to monitor for carryover. When a H-PIN showed carryover, it was eliminated from the mixture and the process was repeated, until the maximum concentration without carryover was found for each H-PIN. The optimized mixture from this step was then used to evaluate the peak shape for each H-PIN from the extracted ion chromatograms. If the peptide elution profile was not optimal (long elution, fronting or tailing) the concentration for that H-PIN was reduced until a suitable elution profile was achieved. The final step in the optimization process was to test the potential effect of H-PINs on peptide identification by DDA in an ion trap mass spectrometer. The glycocapture stock solution, with and without H-PINs, was analyzed via LC/MS/MS in triplicate as set forth in Example 3. The data from each replicate were then pooled and searched by SEQUEST for comparison.

The optimized profile for all H-PINs is shown in FIGS. 1A-1D. The elution times did not exceed one minute for any of the H-PINs. The optimized intensities for the H-PINs were not all in the same range. The amount for the most hydrophobic peptides (H-PINs 9 and 10) had to be reduced to minimize carryover. However, the signal intensities for all H-PINs were well above the noise level (S/N ratio 10 or more). The curated peptide identification from the DDA experiment showed that the number of peptides identified (at a 1.0% false discovery rate, P=0.95) was almost identical with or without the H-PINs present in the sample: 1,010 peptides identifications from the glycocapture stock solution without H-PINs added and 1,018 identifications from the same sample spiked with H-PINs. The optimized concentrations determined for all H-PINs in this manner are listed in Table 2. This set of concentrations was thus used to generate a standard mixture that was used for all experiments (referred to herein as the "H-PIN standard solution").

Example 3

Testing the Effect of H-PINs on Data Dependent Acquisition

A sample of the glycocapture stock solution from Example 1 was analyzed via LC/MS/MS in triplicate. The same experiment was then repeated with a 9 µL sample of the glycocapture stock solution from Example 1 spiked with 1 µL of the H-PIN standard solution from Example 2. The data from each triplicate was then pooled and searched separately using SEQUEST. After data curation using Peptide Prophet (Institute for Systems Biology, Seattle, Wash.), the number of peptides for each dataset with a 2.5% rate of false positives was determined to be 1510 for the glycocapture stock solution sample without H-PINs and 1536 for the glycocapture stock solution sample spiked with H-PINs. This data show that the presence of H-PINs has no negative effect on data dependent acquisition (DDA) experiments.

The elution profile, isotopic distribution and m/z value for all H-PINs separated using a 95 min gradient from 5 to 35% buffer B are shown in FIGS. 1A-1D. The first H-PINs eluted 6 minutes after the first peptides of the glycocapture stock solution (approximately 10% ACN), and the last H-PINs eluted 5 minutes after the last peptides (approximately 65% ACN). Therefore, the whole useful retention time range was covered. The H-PINs eluted sequentially, with the retention time difference between each one being not more than 17 minutes, and not less than 4 minutes. The isotopic distribution was distinctly different for the H-PINs compared to normal peptides (V-shape profile) except for H-PIN 10 for which the first and second isotopic peak had similar intensity. Most H-PINs generated singly, doubly and triply charged ions but in most cases the doubly charged ions were the most intense peak. The m/z values ranged from 345 for H-PIN 6 to 790 for H-PIN 10.

Example 4

Determining the Effect of H-PINS on Protein Identification

One µL of the H-PIN standard solution from Example 2 was spiked into 9 µL of the glycocapture stock solution from Example 1. 1 µL injections of the spiked glycocapture stock solution were then analyzed by LC/MS/MS in triplicate using a 95 min linear gradient from 5 to 35% buffer B. The same experiment was repeated with the glycocapture stock solution lacking the H-PINs. The data for triplicate LC/MS/MS runs with and without H-PINs were searched separately for peptide identifications and comparison. After data curation using Peptide Prophet (Institute for Systems Biology, Seattle, Wash.), the number of proteins for each dataset with a 2.5% rate of false positives was determined to be 358 for the glycocapture stock solution sample without H-PINs and 366 for the glycocapture stock solution sample spiked with H-PINs.

Example 5

Using H-PINS to Detect the Limit of Intensity Normalization and for Relative Quantification (Normalization Quality Control)

This example demonstrates that H-PINs can be used to evaluate limits of normalization performed by quantification algorithms used for label-free proteomics. The statistical packages commonly used for label-free quantifications correct intensity variation by normalizing the entire feature population (see Brusniak, M.-Y., et al., "Computational framework and tools for LC/MS discovery and targeted mass spectrometry-based proteomics", *BMC Bioinf. In press* (2008), which is incorporated herein by reference in its entirety to the extent not inconsistent with the present disclosure). However this process has limitations (see Mueller, L. N., et al., *Proteomics* 7, 3470-80 (2007); Old, W. M., et al., *Mol. Cell. Proteomics* 4, 1487-1502 (2005), which is incorporated herein by reference in its entirety to the extent not inconsistent with the present disclosure) and datasets with variation beyond the statistical ability of the normalizing algorithm can increase the number of false positives significantly.

One µL of the H-PIN standard solution from Example 2 was spiked into 9 µL of the glycocapture stock solution from Example 1. A dilution series was prepared from this spiked stock solution in the following order (1000×, 500×, 100×, 50×, 10×, 5×, 1×) with 1000× being the stock solution. 1 µL of each dilution was injected for LC/MS analysis using a 95 min linear gradient from 5 to 35% buffer B. followed by feature extraction, alignment and normalization using the Super-Hirn-Corra platform (see Brusniak, M.-Y., et al., "Computational framework and tools for LC/MS discovery and targeted mass spectrometry-based proteomics", *BMC Bioinf. In press* (2008), which is incorporated herein by reference in its entirety to the extent not inconsistent with the present disclosure).

Figure 2:
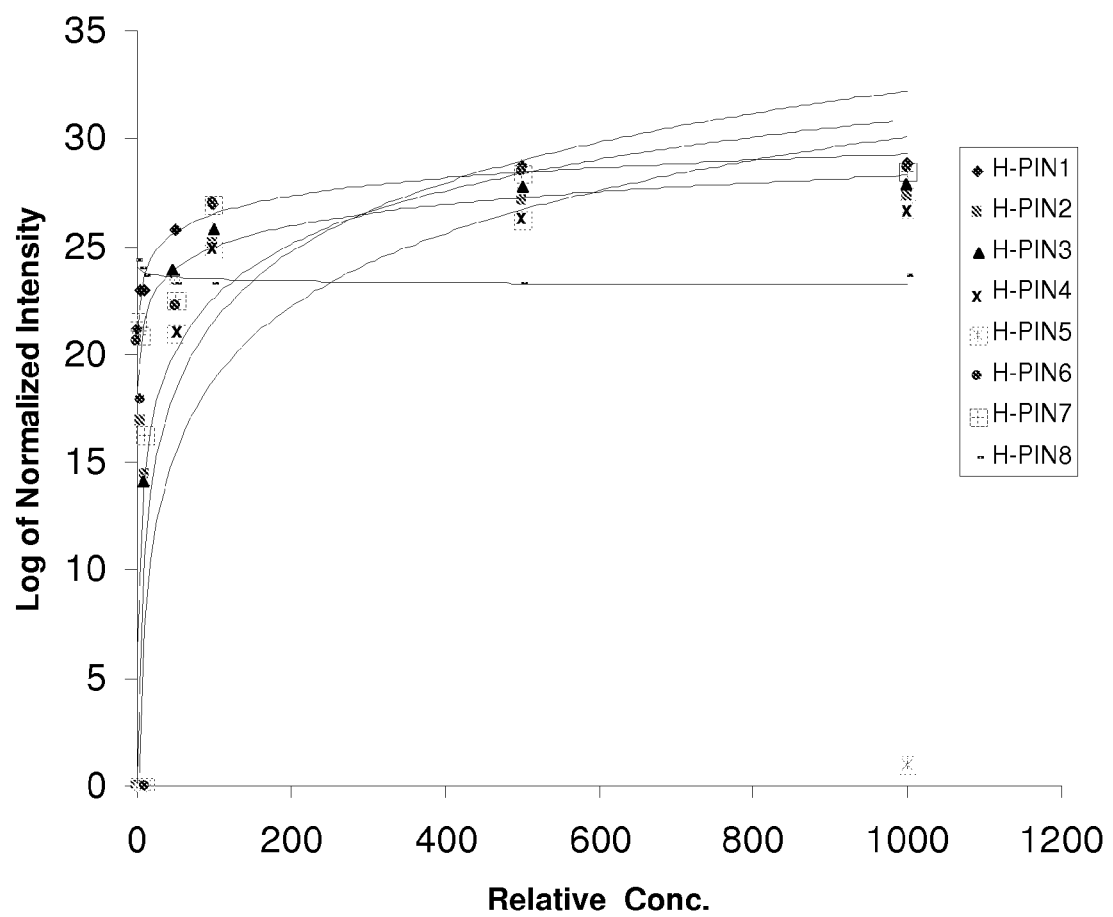
FIG. 2 shows the log of normalized intensities as a function of concentration fold change for representative H-PINs.

The log of the normalized intensities, as a function of concentration fold-change, for 8 H-PINs are shown in FIG. 2 (as discussed below, the last two H-PINs were not used for quantitative measurements). The logarithmic curves were fitted using the curve fitting function in Excel. Almost all the curves followed a similar function, due to normalization.

Based on the curves fitted for all the H-PINs, it was determined that the Corra algorithm could only correct variations of up to 2-fold. For larger variations the signal could not be efficiently compensated by normalization and data with variation beyond this limit cannot be used for label-free quantification. However, as one of skill in the art will appreciate, these limits are platform dependent and need to be established for each platform separately.

Example 6

Using H-PINS for Sample Preparation Quality Control

An important step towards reducing the occurrence of data with variabilities that are beyond the value that can be compensated for by normalization algorithms is to determine the sources of variation and to improve the reproducibility of the system. This Example demonstrates how H-PINs may be used to assess the reproducibility of sample preparation steps.

A dilution series was prepared from the glycocapture stock solution from Example 1 in the following order: 10×, 7.5×, 5×, 2.5×, and 1.25×, with 10× being the stock solution. 1 µL of the H-PIN standard solution from Example 2, was spiked into 9 μL of each glycocapture stock solution dilution to simulate variations in sample preparation. 1 μL of each dilution was injected for LC/MS analysis using a 95 min linear gradient from 5 to 35% buffer B.

Figure 3A:
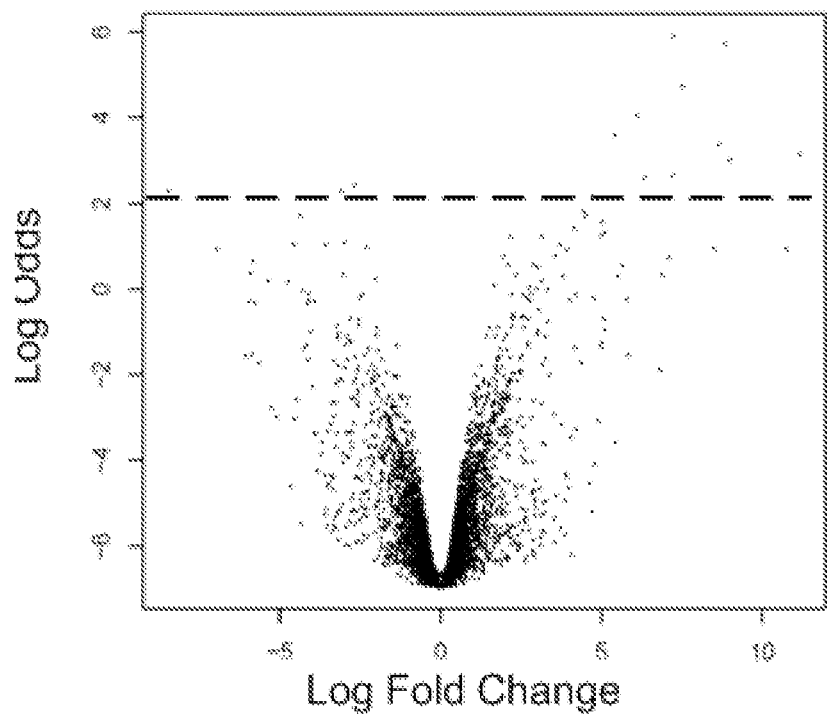
FIGS. 3A-3C show data for sample preparation quality control: a) volcano plot derived from the LC/MS analysis of 5 glycocapture replicates (FIG. 3A), b) Corra algorithm normalizations (FIG. 3B), and c) extracted ion chromatograms (FIG. 3C).
Figure 3B:
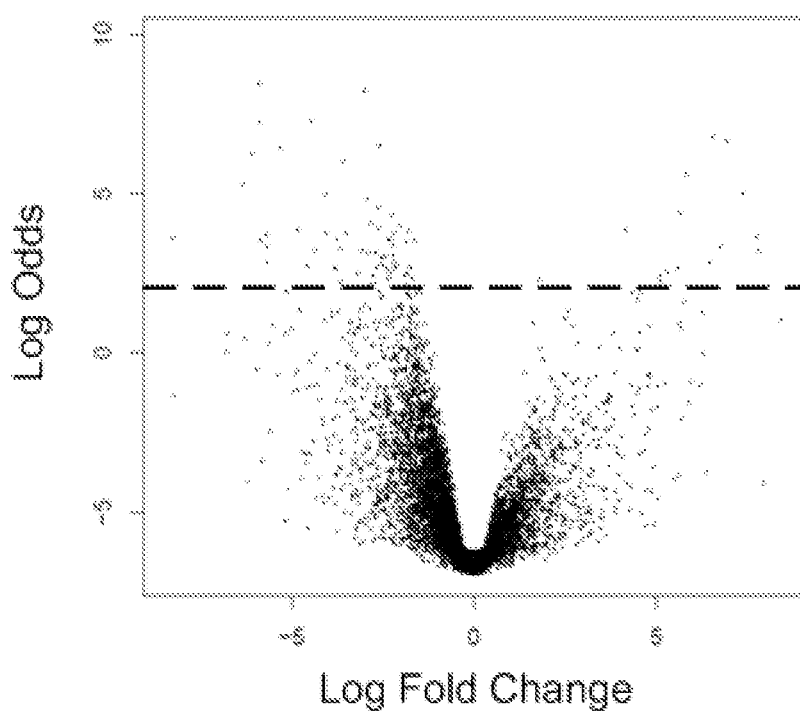

FIG. 3A shows a volcano plot (a plot of fold change vs. the Log odds of a feature being differentially abundant) derived from the LC/MS analysis of the 5 glycocapture stock solution replicates spiked with H-PIN standard solution. Data points above the dotted line represent features with a ≥0.9 probability of being differentially abundant. The number of differentially expressed features found by the SuperHirn-Corra algorithm, in absence of systematic variations, was 14 (in ideal conditions this number should have been zero). FIG. 3B shows the volcano plot derived from the LC/MS analysis of the glycocapture stock solution dilution series spiked with H-PIN standard solution. When 8-fold variations are introduced, the number of differentially abundant features detected increased to 79, even after the normalization performed by Corra algorithm (FIG. 3B). Even though it is easy to detect the increase in the number of differentially abundant features, in practice it is very difficult to find the source of variation. However, with the use of H-PINs as internal standards, the root cause of variation could be diagnosed, as described below.

Figure 3C:
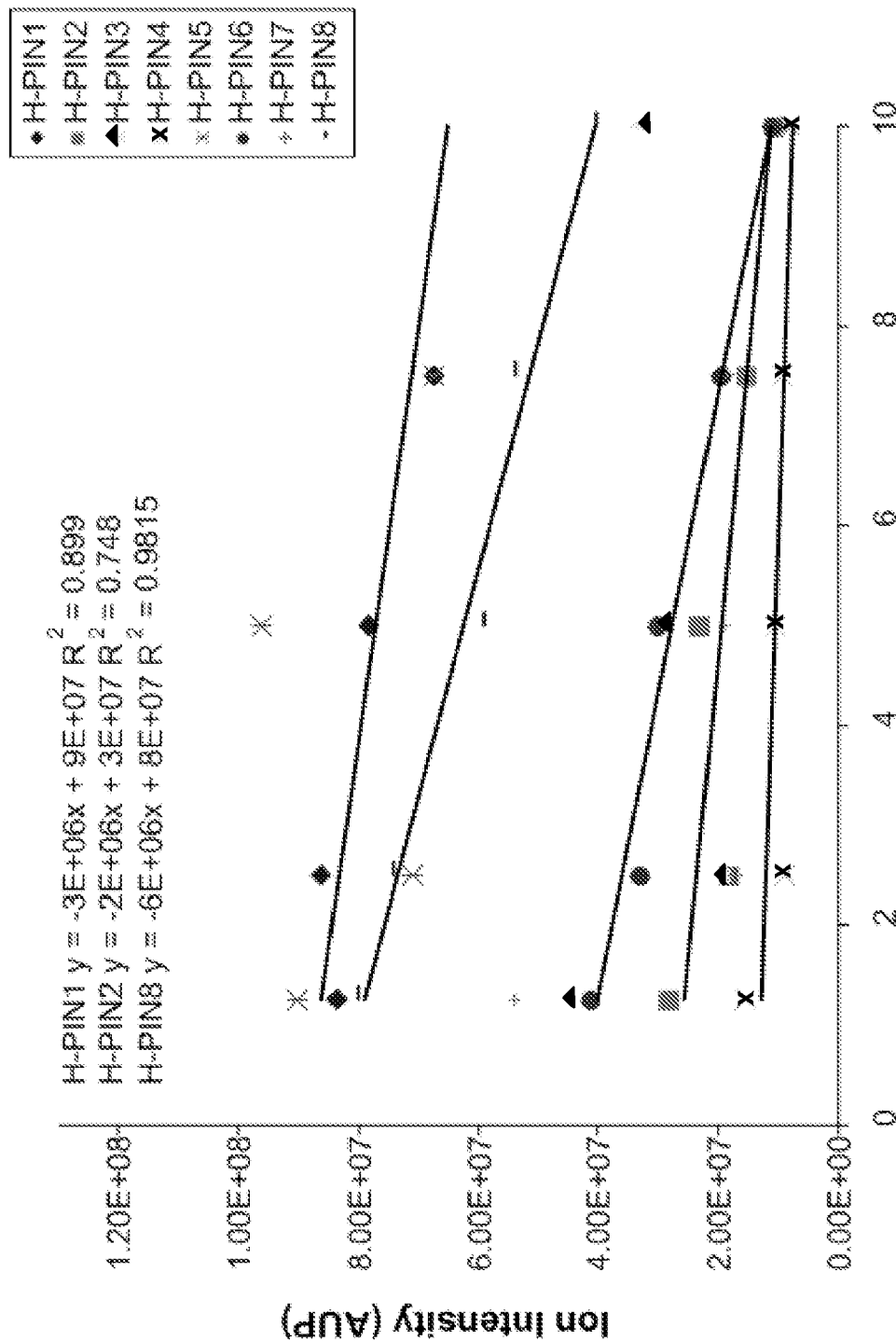

The mass spectral response (area under the curve) for H-PINs plotted vs. the concentration fold change is shown in FIG. 3C. The H-PINs were quantified by using the area under the peak from their extracted ion chromatograms (FIG. 3C). The non-normalized intensities for most H-PINs were quite similar across all runs with a slight negative slope due to differential ion suppression. The H-PINs behavior indicated that HPLC systems and mass spectrometers were working properly, and the variation occurred pre-LC/MS. This conclusion was made based on the fact that while significant change in the number of differentially abundant features was detected, the signal intensity from H-PINs which were added after sample preparation remained almost constant. In addition, these results demonstrated the impact of sample preparation errors on the false positive rate, further emphasizing the need for a robust quality control method such as H-PINs Example 7

Using H-PINS for LC/MS Quality Control

This Example demonstrates that H-PINs can be used to assess the performance of LC/MS instruments and to determine whether instrumental analysis is a major source of variation. In this regard, significant variation may be introduced during LC/MS analysis due to changes in sample concentration (e.g., via sample evaporation), mis-injection (e.g., clogged needle, clogged sample loop, etc.), and irreproducible trapping (e.g., damaged trap, or irreproducible solvent delivery).

One μL of the H-PIN standard solution from Example 2 was spiked into 9 μL of the glycocapture stock solution from Example 1. A dilution series was prepared from this stock solution in the following order (10×, 7.5×, 5×, 2.5×, and 1.25×) with 10× being the stock solution to simulate data acquired by an irreproducible LC/MS. 1 μL of each dilution was injected for LC/MS analysis in a 95 min linear gradient from 5 to 35% buffer B.

Figure 4A:
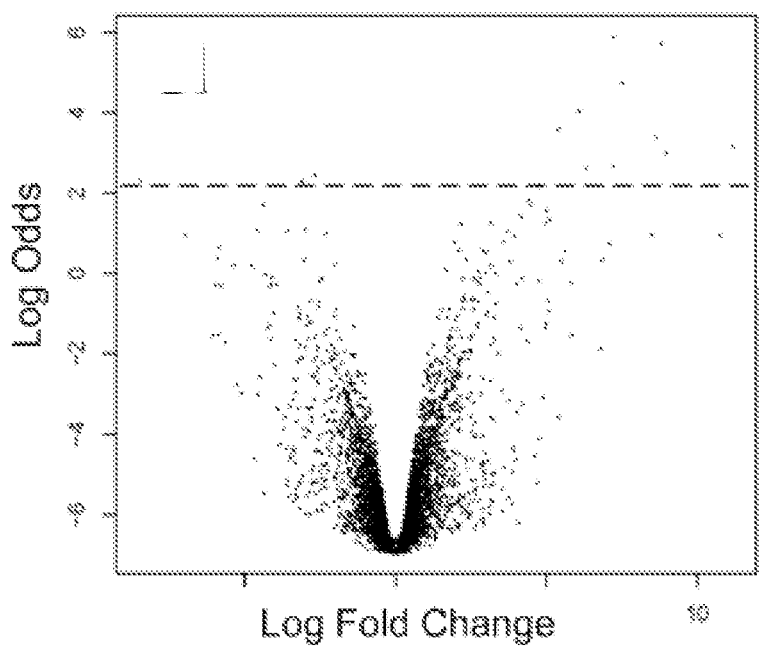
FIGS. 4A-4C show data for LC/MS quality control: a) volcano plot derived from the LC/MS analysis of 5 glycocapture replicates (FIG. 4A), b) Corra algorithm normalizations (FIG. 4B), and c) extracted ion chromatograms (FIG. 4C).
Figure 4B:
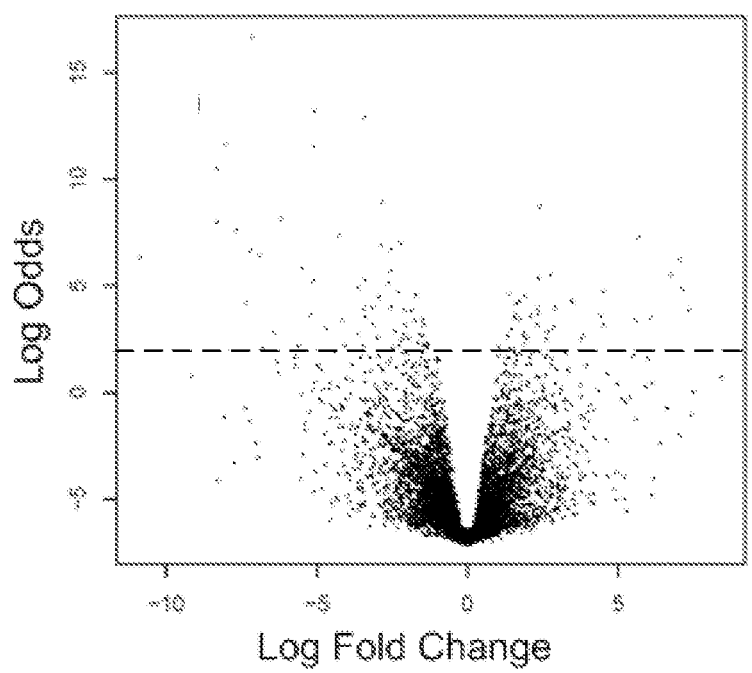

FIG. 4A shows the volcano plot derived from the LC/MS analysis of the 5 glycocapture stock solution replicates. When an 8-fold variation was introduced, the number of differentially expressed features increased 7 fold (total of 97 vs. 14) (FIG. 4B). While a significant increase in the number of differentially expressed features can be easily detected, the source of the variation is not easy to pinpoint in practice. Mass spectral signals generated by H-PINs can be used for such diagnosis as described below.

Figure 4C:
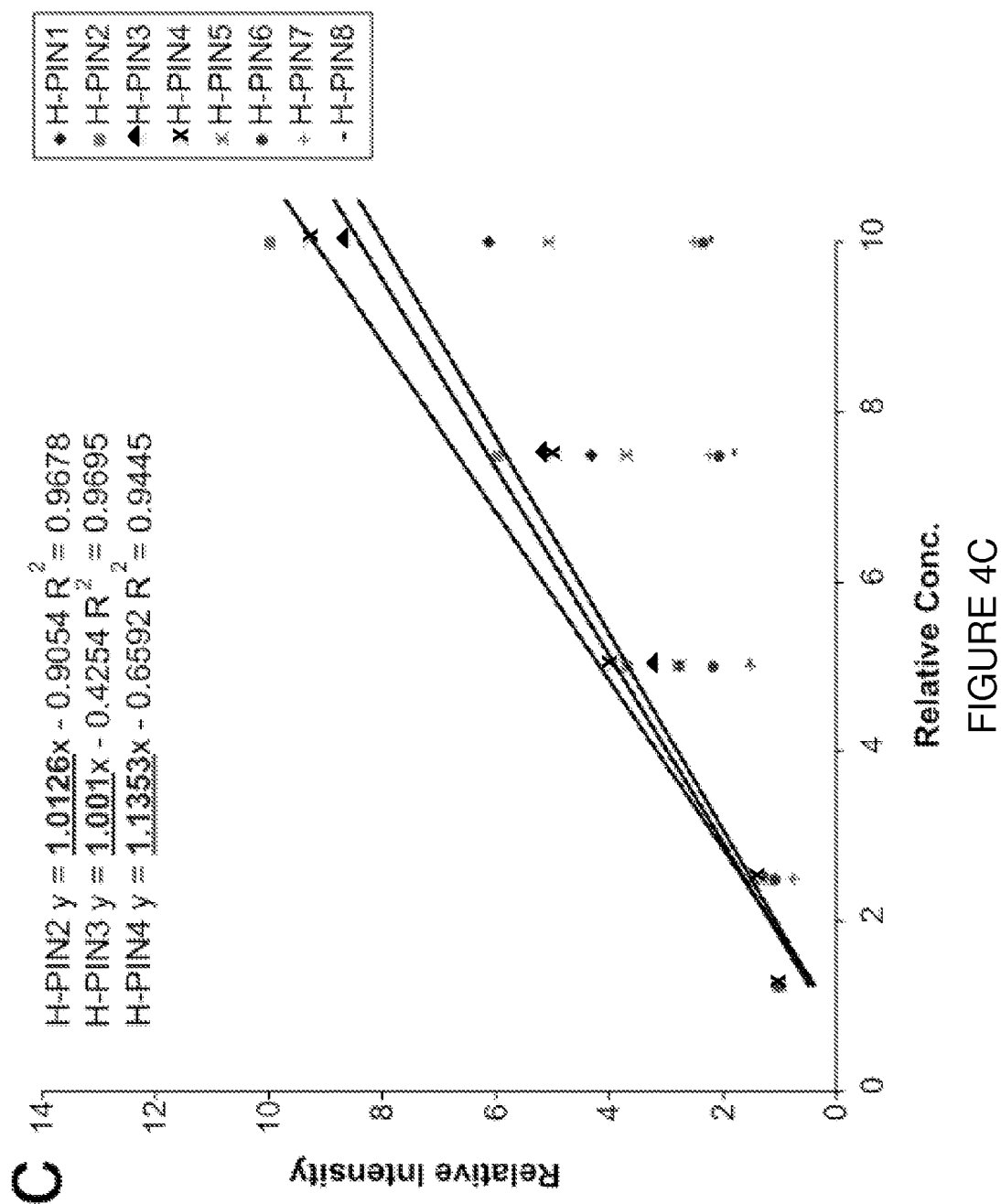

The intensity fold change vs. injection variation plot for H-PINs is shown in FIG. 4C. The intensity fold change for each H-PINs was calculated by measuring the area under the peak for that H-PINs in each dilution, divided by the area under the curve for the same H-PINs in the least concentrated sample (FIG. 4C). All H-PINs showed a trend of increasing intensity as expected. The goal of this experiment was to show that irreproducibility in LC/MS performance could be detected if significant changes in signal intensity of H-PINs, added right before LC/MS analysis, were observed. Such irreproducibility was simulated by having a dilution series, however, in practice such variations would be introduced as a result of poor LC/MS performance. Although all H-PINs did not show the same response sensitivity, H-PINs 1, 3 and 4 in particular were quite sensitive and could be used directly to measure the variation introduced by LC/MS.

Example 8

Using H-PINS for Mass Calibration of the Mass Spectrometer

When large sets of data are generated it is not desirable to stop and calibrate instruments every day for reproducibility reasons. However, running mass spectrometers without daily calibration can affect the mass accuracy. This example demonstrates the utility of H-PINs for post-acquisition mass calibration (see Balough, M., *Spectroscopy* 19:34-38 (2004), which is incorporated herein by reference in its entirety to the extent not inconsistent with the present disclosure).

Mis-calibrated mass spectra were generated using the RecalOffline functionality of Xcalibur software (Thermo-Finnigan, San Jose, Calif.). The H-PIN 5 doubly charged ion was used as an anchor for mis-calibration and all mass spectral features from all scans were shifted accordingly. Five mis-calibrated LC/MS/MS runs were generated with mass shifting s equal to 1.0, 0.75, 0.5, 0.25, and 0.125 Da. For recalibration, LC/MS/MS total ion chromatograms (TIC) were sliced into 10 shorter TICs each including a single H-PIN in the middle using the RecalOffline function. The TIC was sliced between each pair of H-PINs in the middle, and each slice was calibrated separately using the residing H-PIN's mass to charge ratio. Calibrated TIC slices were then converted to mzXML format and searched separately (see Pedrioli, P. G. A., et al., *Nature Biotechnology* 22(11):1459-1466 (2004), which is incorporated herein by reference in its entirety to the extent not inconsistent with the present disclosure). The search results were then combined for PeptideProphet interaction (see Keller, A., et al., *Anal. Chem.* 74(20): 5383-92 (2002), which is incorporated herein by reference in its entirety to the extent not inconsistent with the present disclosure).

The numbers of unique peptides and proteins, at equal false discovery rates of 1.2% were compared for all files (Table 1). The result showed that mass variations as small as 0.125 Da (60 ppm for a doubly charged ion at 541.22 mass) can lead to 8% difference in the number of confident protein identifications. This result also demonstrated that even with a well-calibrated instrument, H-PIN assisted post-acquisition recalibration can result in significant improvement in positive protein identifications (7%). Significant decrease in the number of IDs was observed as the deviation from mass accuracy was increased. These data show that, even in the most stable systems, H-PINs can be effectively used for post analysis mass calibration. Furthermore, for data with inferior mass accuracy the results may be more dramatic.

TABLE 1

Number of Peptides and Proteins Identified With P = 0.95 From Calibrated, Re-calibrated and Mis-Calibrated LC/MS/MS Data

| Mass Deviation | Unique Peptide IDs | Unique Protein IDs | % Decrease of Protein ID |
|---|---|---|---|
| Re-Calibrated | 662 | 143 | 0% |
| Well-Calibrated | 721 | 134 | 7% |
| 0.125 Da | 646 | 132 | 8% |
| 0.250 Da | 584 | 122 | 17% |
| 0.500 Da | 443 | 103 | 30% |
| 0.750 Da | 179 | 49 | 190% |
| 1.000 Da | 63 | 22 | 550% |

Example 9

Using H-PINS to Synchronize Retention Times Between Different Chromatography Instruments While precursor and fragment ion masses can easily be transferred between instruments, e.g., from a fast scanning mass spectrometer to an S/MRM-capable instrument such as a triple quadrupole MS, retention times are more difficult to correlate, due to the less-reproducible nature of chromatography (see Stahl-Zeng, J., et al., *Mol. Cell. Proteomics* 6, 1809-1817 (2007), which is incorporated herein by reference in its entirety to the extent not inconsistent with the present disclosure). This Example demonstrates how H-PINs can be used to synchronize the retention times between two different LC systems for scheduled S/MRM.

Multiple transitions were generated for each H-PIN using the TIQAM algorithm (see Lange, V., et al., *Molecular & Cellular Proteomics* 7(8):1489-1500 (2008), which is incorporated herein by reference in its entirety to the extent not inconsistent with the present disclosure) and were validated by injecting 5 μL of an H-PIN cocktail containing 10× the maximum injectable amount for LC/MRM analysis. The most intense transitions for each H-PIN were found and used for retention time determination (Table 3). S/MRM transitions were generated from LC/MS/MS data acquired by analyzing 1 μL of spiked glycocapture stock solution (1 μL of 10× maximum injectable H-PINs cocktail in 9 μL of the glycocapture stock solution from Example 1) using SpectraST algorithm (see Lam, H., et al., *Proteomics* 7(5):655-667 (2007), which is incorporated herein by reference in its entirety to the extent not inconsistent with the present disclosure). H-PIN features were then extracted from the LC/MS/MS ion chromatogram using Xcalibur Qual browser (available from Thermo-Finnigan) to determine their retention time. The retention times of the extracted S/MRM transitions were synchronized using the H-PIN retention times from LC/MS/MS and S/MRM traces and monitored via scheduled S/MRM (see Lange, V., et al., *Mol. Cell. Proteomics* 7, 1489-1500 (2008); Stahl-Zeng, J., et al., *Mol. Cell. Proteomics* 6, 1809-1817 (2007), which are incorporated herein by reference in their entireties to the extent not inconsistent with the present disclosure) and the following formula:

$$RT(MS)_{HPIN_{i-1}} \leq \forall RT(MS)_{feature_x} \leq RT(MS)_{HPIN_i} RT$$
$$(MRM)_{feature_x} = ((RT(MRM)_{HPIN_i}/RT(MS)HPIN_i) \cdot (RT(MS)_{feature_x} - RT(MS)_{HPIN_{i-1}})) + RT(MRM)_{HPIN_{i-1}}$$

wherein:

$RT(MS)_{feature}$ is the retention time of the unknown feature on the MS system;

$RT(MRM)_{feature}$ is the retention time of the unknown feature on the MRM system, $RT(MS)_{HPINi}$ is the retention time of H-PIN #i on the MS system;

$RT(MS)_{HpiNi-1}$ is the retention time of H-PIN #i-1 on the MS system $RT(MRM)_{HPINi}$ is the retention time of H-PIN #i on the MRM system;

$RT(MRM)_{HinNi-1}$ is the retention time of the H-PIN eluting before H-PIN #i on the MRM system; and the retention time of the unknown feature is between the retention times of H-PIN$_{i-1}$ and H-PIN$_i$.

Figures 5A, 5C:
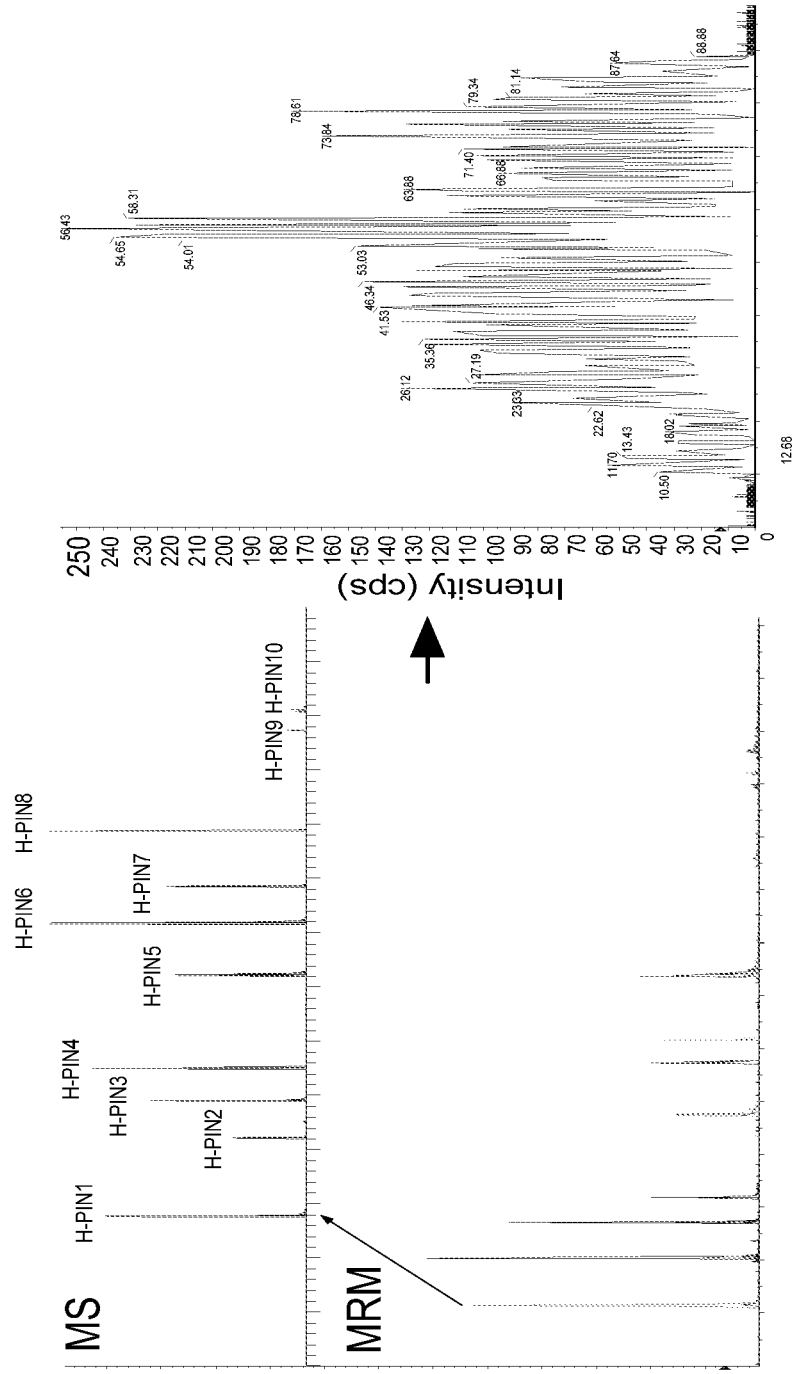
FIGS. 5A-5D show data for synchronization of retention times between different chromatography instruments: a) dead volume match (FIG. 5A), b) full synchronization (FIG. 5B), c) scheduled MRM for 280 transitions using retention time shift (FIG. 5C), and d) scheduled MRM for 280 transitions using synchronized retention time shift (FIG. 5D).

The success of the synchronization process was then tested in the following experiment. The retention times of 280 transitions were adjusted first by matching the dead volume between the two LC systems to examine the adequacy of such approach (FIG. 5A). Then full retention time synchronization was performed using the formula described above (FIG. 5B). These 280 transitions were monitored via scheduled MRM using both sets of retention time.

Next the accuracy of synchronized retention times was determined. Synchronization accuracy determines the percentage of synchronized retention times that are close enough to their true value that are detected within the allowed retention time window. To test the accuracy the model, a set of 235 transitions were monitored using scheduled S/MRM with synchronized retention time and five minutes scan time for each peptide. The same set of peptides were monitored using unscheduled S/MRM (in unscheduled MRM, transitions are constantly monitored for the duration of the acquisition time). The goal of the experiment was to find if any of the peptides found in unscheduled MRM were missing from synchronized scheduled MRM.

Figures 5B, 5D:
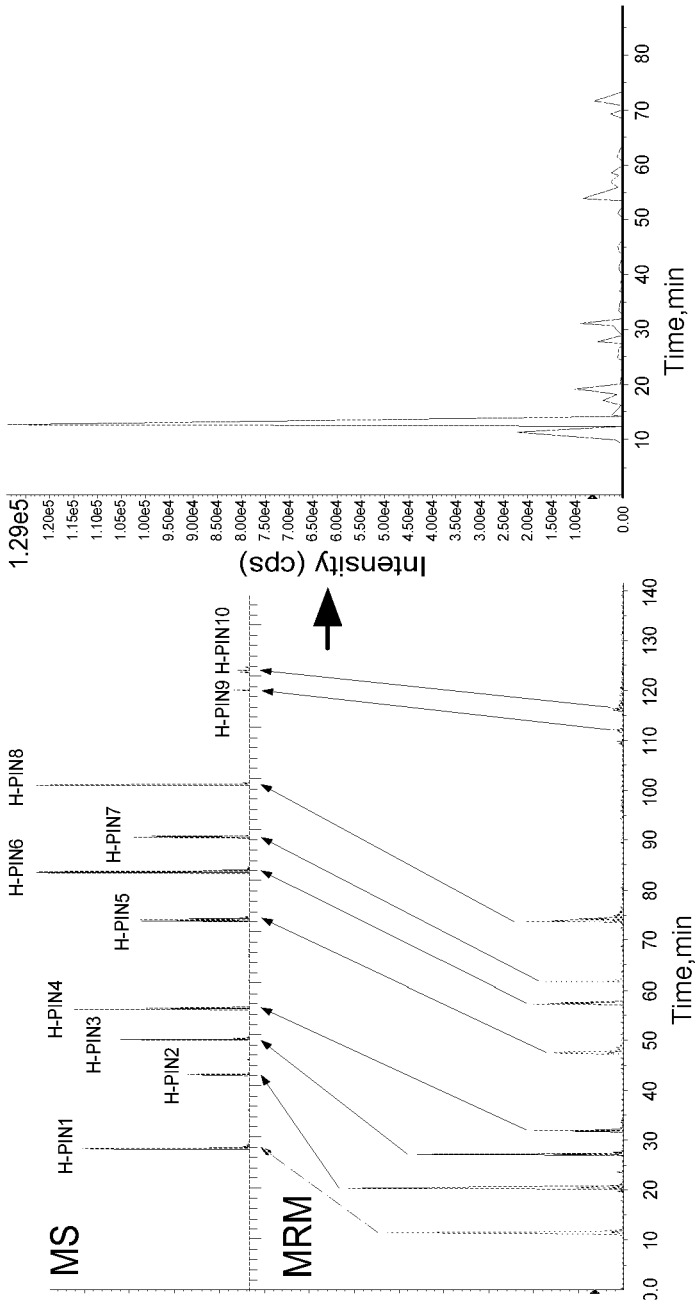
Figure 6:
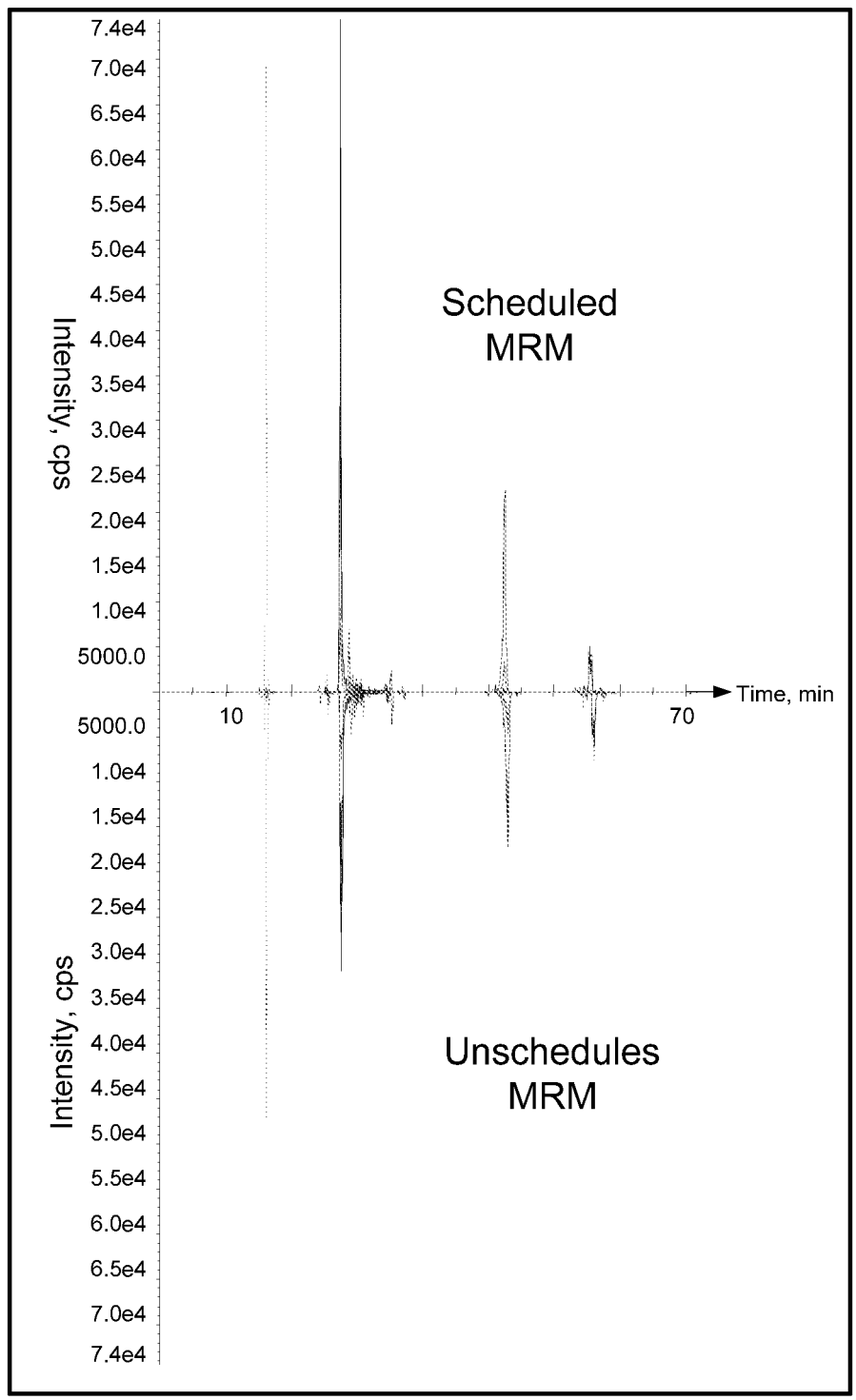
FIG. 6 shows a set of 235 transitions monitored using scheduled MRM with synchronized retention times as well as unscheduled MRM.

The results from the first experiment showed that, without full synchronization, no transition will be detected (FIGS. 5C and 5D). This means that retention times are dynamic values that change unproportionately and for full synchronization, multiple retention time gauges are required. The accuracy of the synchronization process was determined by monitoring large number of transitions with and without scheduling. The results showed that not only no peptide was missing from the scheduled run, but also the intensities were higher, due to the longer dwell times in the scheduled mode (FIG. 6).

Overall, these experiments showed that H-PINs may be usefully used for retention time transfer between various instruments without sacrificing transitions in scheduled mode. In addition, H-PINs can be used to monitor instrument drifting and retention time shifts caused by instrument aging and repair.

Example 10

Using H-PINS to Monitor the Performance of Chromatography Columns

One source of variation in liquid chromatography comes from inconsistencies in the performance of liquid chromatography columns, especially capillary columns used in nano-LC/MS. Since a high degree of retention time reproducibility is essential for label-free quantification, frequent replacement of a chromatography column is not desirable. On the other hand, using a deteriorating column could have an adverse effect on the reproducibility. Deteriorating columns have common symptoms, such as increased back pressure and loss of resolution which negatively impact peptide detection, mainly due to irreversible absorption of hydrophobic compounds, which bleed off the resin and leave a trace at the high organic end of the gradient. Two of the H-PINs (H-PINs 9 and 10) are quite hydrophobic, and elute very late in this high organic region of the gradient. Observations showed that the ionization of these H-PINs was suppressed by such hydrophobic contaminants, and, as a result, the performance of a liquid chromatography column can be monitored by monitoring the ionization of these two H-PINs. Based on observations, more than a 10 fold decrease in the intensity of the extracted ion chromatogram for these peptides indicates column deterioration.

Example 11

Representative H-PINS

Table 2 shows representative H-PIN sequences (SEQ ID NOS:1-10, in order of appearance) and their corresponding molecular formulae (MF), molecular weight (MW), optimized concentration (see Example 2), and mass to charge (m/z) values of three different charge states. The structures of these representative H-PINs are shown following Table 2.

TABLE 2

Representative H-PINs

| H-PIN | Sequence | MF | MW | Conc. (fM/μl) | m/z (Charge) |
|---|---|---|---|---|---|
| 1 | H-D-4-bromo-Phe-Lys(Me)$_3$-Arg-Tyr-Gly-OH | $C_{35}H_{52}N_9O_7Br$ | 789.3173 | 85 | 790.3252 (1+) 395.6666 (2+) 264.4496 (3+) |
| 2 | H-D-4-bromo-Phe-Lys(Me)$_3$-Gly-Arg-Tyr-Tyr-OH | $C_{44}H_{61}N_{10}O_9Br$ | 952.3806 | 64 | 953.3885 (1+) 477.1982 (2+) 318.8040 (3+) |
| 3 | H-D-4-bromo-Phe-Lys(Me)$_3$-Arg-Tyr-Gly-Tyr-Val-OH | $C_{49}H_{70}N_{11}O_{10}Br$ | 1051.449 | 44 | 1052.4570 (1+) 526.7324 (2+) 351.8268 (3+) |
| 4 | H-D-4-bromo-Phe-Lys(Me)$_3$-Gly-Arg-Tyr-Tyr-Val-Tyr-OH | $C_{58}H_{79}N_{12}O_{12}Br$ | 1214.512 | 42 | 1215.52 (1+) 608.2641 (2+) 406.1813 (3+) |
| 5 | H-His-p-chloro-Phe-p-chloro-phe-p-chloro-Phe-Ala-Ala-OH | $C_{51}H_{67}N_{12}O_8Cl_3$ | 1080.427 | 36 | 1081.4350 (1+) 541.2214 (2+) 361.4862 (3+) |
| 6 | H-4-chloro-Phe-4-chloro-Phe-4-chloro-Phe-Lys-NH$_2$ | $C_{33}H_{39}N_6O_4Cl_3$ | 688.2098 | 35 | 689.2177 (1+) 345.1128 (2+) 230.7471 (3+) |
| 7 | H-Ala-p-chloro-Phe-p-chloro-Phe-p-chloro-Phe-Ala-Ala-Ala-Lys-NH$_2$ | $C_{45}H_{59}N_{10}O_8Cl_3$ | 972.3582 | 34 | 973.3661 (1+) 487.1870 (2+) 325.46326 (3+) |
| 8 | H-Ile-Ile-p-chloro-Phe-p-chloro-Phe-p-chloro-Phe-Ala-Ala-Lys-NH$_2$ | $C_{51}H_{71}N_{10}O_8Cl_3$ | 1056.452 | 27 | 1057.4594 (1+) 529.2340 (2+) 353.4945 (3+) |
| 9 | H-Ile-Ile-p-chloro-Phe-p-chloro-Phe-p-chloro-Phe-Ile-Ile-Ala-Ala-Ala-Ala-Lys-NH$_2$ | $C_{69}H_{103}N_{14}O_{12}Cl_3$ | 1424.695 | 19 | 1425.702 (1+) 713.3552 (2+) 476.24203 (3+) |

TABLE 2-continued
Representative H-PINs
| H-PIN | Sequence | MF | MW | Conc. (fM/μl) | m/z (Charge) |
|---|---|---|---|---|---|
| 10 | H-Ile-Ile-Ile-p-chloro-Phe-p-chloro-Phe-p-chloro-Phe-Ile-Ile-Ile-Ala-Ala-Ala-Lys-NH$_2$ | $C_{78}H_{120}N_{15}O_{13}Cl_3$ | 1579.826 | 16 | 1580.833 (1+) 790.9207 (2+) 527.95236 (3+) |
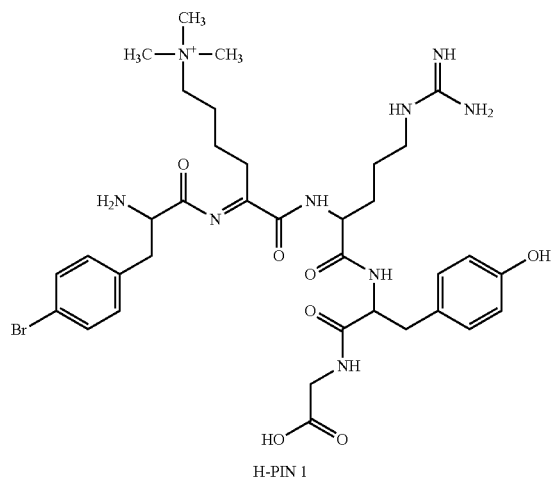 [SMILES: C[N+](C)(C)CCCC/C(=N\C(=O)C(N)Cc1ccc(Br)cc1)C(=O)NC(CCCNC(=N)N)C(=O)NC(Cc1ccc(O)cc1)C(=O)NCC(=O)O]
H-PIN 1
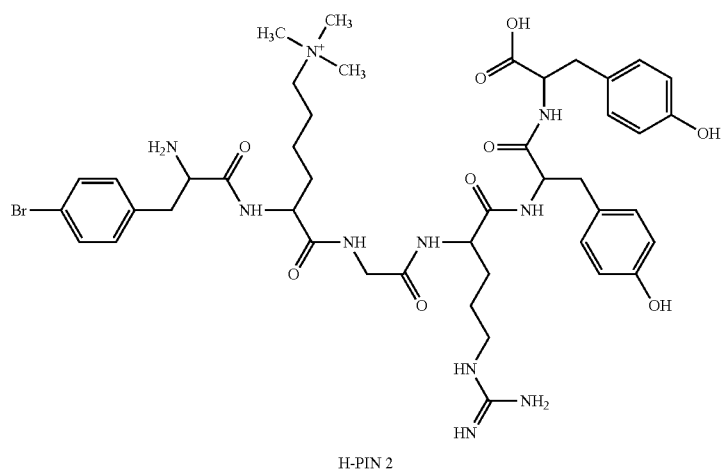 [SMILES: C[N+](C)(C)CCCCC(NC(=O)C(N)Cc1ccc(Br)cc1)C(=O)NCC(=O)NC(CCCNC(=N)N)C(=O)NC(Cc1ccc(O)cc1)C(=O)NC(Cc1ccc(O)cc1)C(=O)O]
H-PIN 2

TABLE 2-continued
Representative H-PINs
| H-PIN | Sequence | MF | MW | Conc. (fM/µl) | m/z (Charge) |
|-------|----------|----|----|---------------|--------------|
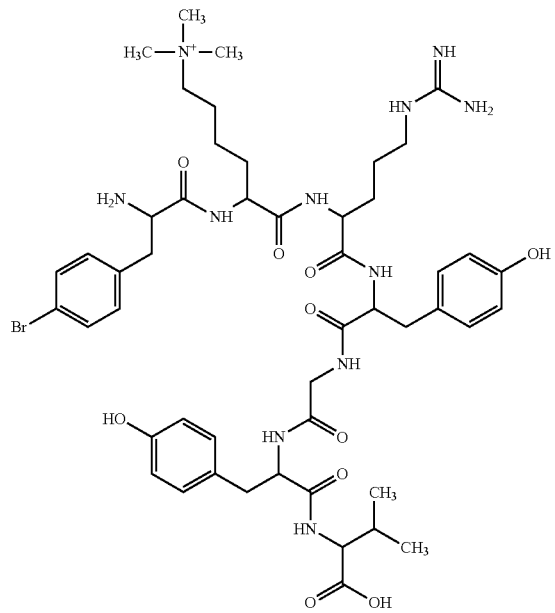
H-PIN 3
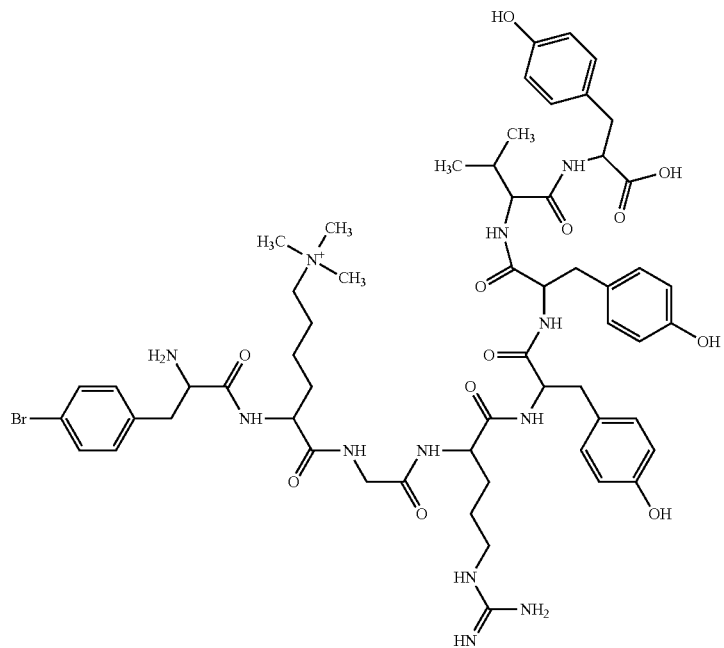
H-PIN 4

TABLE 2-continued

| | | Representative H-PINs | | | |
|---|---|---|---|---|---|
| H-PIN | Sequence | MF | MW | Conc. (fM/μl) | m/z (Charge) |

H-PIN 5

H-PIN 6

H-PIN 7

TABLE 2-continued

Representative H-PINs

| H-PIN | Sequence | MF | MW | Conc. (fM/μl) | m/z (Charge) |
|-------|----------|-----|-----|---------------|--------------|

H-PIN 8

H-PIN 9

H-PIN 10

Example 12

Retention Times, Transitions, and Collision Energies for Representative H-PINS Table 3 shows retention times for representative H-PINs from LC/MS (RT(MS)) and MRM (RT(MRM)) 60 min. runs as well as the most intense transitions (Q1/Q3) and collision energies (CE).

TABLE 3

Retention Times, Transitions, and Collision Energies for Representative H-PINs

| H-PIN | RT(MS) | RT(MRM) | Q1/Q3 | | CE |
|---|---|---|---|---|---|
| 1 | 27.91 | 11.19 | 264.1136 | 396.1287 | 13.96979 |
|   |       |       | 264.1136 | 395.2043 | 13.96979 |
| 2 | 42.45 | 20.54 | 477.1981 | 345.1451 | 26.49672 |
|   |       |       | 318.468  | 345.1451 | 16.74187 |
|   |       |       | 318.468  | 501.2462 | 16.74187 |
|   |       |       | 318.468  | 558.2676 | 16.74187 |
| 3 | 49.25 | 26.92 | 526.7323 | 477.15   | 28.67622 |
|   |       |       | 351.4908 | 396.1287 | 18.42603 |
|   |       |       | 351.4908 | 772.3146 | 18.42603 |
|   |       |       | 526.7323 | 657.336  | 28.67622 |
|   |       |       | 351.4908 | 281.1501 | 18.42603 |
| 4 | 55.20 | 32.33 | 608.264  | 820.3994 | 32.26362 |
|   |       |       | 405.8453 | 607.2768 | 21.19811 |
|   |       |       | 405.8453 | 820.3994 | 21.19811 |
|   |       |       | 405.8453 | 281.1501 | 21.19811 |
| 5 | 72.56 | 47.54 | 541.2213 | 318.1122 | 29.31374 |
|   |       |       | 361.1502 | 499.1416 | 18.91866 |
|   |       |       | 541.2213 | 583.3011 | 29.31374 |
|   |       |       | 541.2213 | 764.3305 | 29.31374 |
|   |       |       | 541.2213 | 945.3599 | 29.31374 |
|   |       |       | 361.1502 | 260.1974 | 18.91866 |
| 6 | 81.90 | 55.90 | 345.1127 | 259.16   | 20.68496 |
|   |       |       | 345.1127 | 509.1722 | 20.68496 |
| 7 | 88.82 | 62.82 | 487.187  | 541.2541 | 26.93623 |
|   |       |       | 487.187  | 722.2836 | 26.93623 |
|   |       |       | 487.187  | 903.313  | 26.93623 |
|   |       |       | 487.187  | 360.2247 | 26.93623 |
| 8 | 99.04 | 73.17 | 529.2339 | 185.1    | 28.78629 |
|   |       |       | 529.2339 | 477.15   | 28.78629 |
|   |       |       | 529.2339 | 651.2464 | 28.78629 |
|   |       |       | 529.2339 | 832.2759 | 28.78629 |
|   |       |       | 529.2339 | 945.3599 | 28.78629 |
|   |       |       | 529.2339 | 470.217  | 28.78629 |
| 9 | 117.63 | 111.44 | 713.3551 | 838.4593 | 36.88762 |
|   |       |        | 713.3551 | 1200.518 | 36.88762 |
|   |       |        | 713.3551 | 657.4299 | 36.88762 |
|   |       |        | 475.906  | 544.3459 | 24.77121 |
|   |       |        | 475.906  | 657.4299 | 24.77121 |
| 10 | 121.51 | 115.92 | 790.9206 | 880.5063 | 40.30051 |
|    |        |        | 790.9206 | 1061.536 | 40.30051 |
|    |        |        | 790.9206 | 1242.565 | 40.30051 |
|    |        |        | 790.9206 | 1355.649 | 40.30051 |
|    |        |        | 790.9206 | 699.4769 | 40.30051 |
|    |        |        | 527.6163 | 586.3928 | 27.40843 |

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A method for identifying and quantifying a peptide in a sample, the method comprising:
   (a) adding a plurality of halogenated peptide standards to the sample as internal standards;
   (b) analyzing the sample containing said internal standards using liquid chromatography-mass spectrometry;
   (c) identifying the liquid chromatography-mass spectrometry data which correspond to the peptide;
   (d) identifying the liquid chromatography-mass spectrometry data which correspond to the halogenated peptide standards; and
   (e) quantifying the amount of the peptide in the sample using the data identified in steps (c) and (d),
   wherein in said halogenated peptides, said halogens are selected from chlorine and bromine, that replace one or more hydrogens in an amino acid, and
   wherein each halogenated amino acid residue is halogenated phenylalanine.

2. A method for monitoring performance of a liquid chromatography-mass spectrometry system, the method comprising:
   (a) adding a plurality of halogenated peptide standards to a sample as internal standards;
   (b) analyzing the sample containing said internal standards using the liquid chromatography-mass spectrometry system;
   (c) identifying the liquid chromatography-mass spectrometry data which correspond to the halogenated peptide standards;
   (d) using the data identified in step (c) to conduct a quality control assessment of the liquid chromatography-mass spectrometry system or to calibrate the liquid chromatography-mass spectrometry system,
   wherein in said halogenated peptides, said halogens are selected from chlorine and bromine, that replace one or more hydrogens in an amino acid, and
   wherein each halogenated amino acid residue is halogenated phenylalanine.

3. The method of claim 2 wherein step (d) further comprises using the data identified in step (c) to:
   (i) determine the limit of an intensity normalization process used with the liquid chromatography-mass spectrometry system and eliminate liquid chromatography-mass spectrometry data with variations beyond the limit;
   (ii) determine whether variation in liquid chromatography-mass spectrometry system data of the liquid chromatography-mass spectrometry system is due to sample preparation or performance of the liquid-chromatography-mass spectrometry system;
   (iii) to recalibrate mis-calibrated liquid chromatography-mass spectrometry data;
   (iv) monitor the performance of a liquid chromatography column of the liquid chromatography-mass spectrometry system; or
   (v) synchronize the retention times between a first liquid chromatography system and a second liquid chromatography system of the liquid chromatography-mass spectrometry system.

4. The method of claim 1, wherein each halogenated peptide standard independently comprises from about 2 to about 20 amino acids residues.

5. The method of claim 1, wherein each halogenated amino acid residue is independently 4-chlorophenylalanine or 4-bromophenylalanine.

6. The method of claim 1, wherein each halogenated peptide standard independently comprises D amino acid residues.

7. The method of claim 1 wherein the sample is a biological sample.

8. The method of claim 7, wherein the biological sample is a body fluid, secreted proteins, cell surface proteins, plant-derived material, or a microorganism.

9. The method of claim 8, wherein the biological sample is human plasma.

10. The method of claim 2, wherein each halogenated peptide standard independently comprises from about 2 to about 20 amino acids residues.

11. The method of claim 2, wherein each halogenated amino acid residue is independently 4-chlorophenylalanine or 4-bromophenylalanine.

12. The method of claim 2, wherein each halogenated peptide standard independently comprises D amino acid residues.

13. The method of claim 2 wherein the sample is a biological sample.

14. The method of claim 13, wherein the biological sample is a body fluid, secreted proteins, cell surface proteins, plant-derived material, or a microorganism.

15. The method of claim 14, wherein the biological sample is human plasma.

16. A method for identifying and quantifying a peptide in a sample, the method comprising:
(a) adding a plurality of halogenated peptide standards to the sample as internal standards;
(b) analyzing the sample containing said internal standards using liquid chromatography-mass spectrometry;
(c) identifying the liquid chromatography-mass spectrometry data which correspond to the peptide;
(d) identifying the liquid chromatography-mass spectrometry data which correspond to the halogenated peptide standards; and
(e) quantifying the amount of the peptide in the sample using the data identified in steps (c) and (d),
wherein in said halogenated peptides, said halogens are selected from chlorine and bromine, that replace one or more hydrogens in an amino acid, and
wherein at least one of the halogenated peptide standards comprises a halogenated amino acid residue at the N-terminus and/or at the carboxyl terminus.

17. The method of claim 16, wherein each halogenated peptide standard independently comprises from about 2 to about 20 amino acids residues.

18. The method of claim 17, wherein each halogenated peptide standard independently comprises D amino acid residues.

19. The method of claim 17 wherein the sample is a biological sample.

20. The method of claim 19, wherein the biological sample is a body fluid, secreted proteins, cell surface proteins, plant-derived material, or a microorganism.

21. The method of claim 20, wherein the biological sample is human plasma.

22. A method for monitoring performance of a liquid chromatography-mass spectrometry system, the method comprising:
(a) adding a plurality of halogenated peptide standards to a sample as internal standards;
(b) analyzing the sample containing said internal standards using the liquid chromatography-mass spectrometry system;
(c) identifying the liquid chromatography-mass spectrometry data which correspond to the halogenated peptide standards;
(d) using the data identified in step (c) to conduct a quality control assessment of the liquid chromatography-mass spectrometry system or to calibrate the liquid chromatography-mass spectrometry system,
wherein in said halogenated peptides, said halogens are selected from chlorine and bromine, that replace one or more hydrogens in an amino acid, and
wherein at least one of the halogenated peptide standards comprises a halogenated amino acid residue at the N-terminus and/or at the carboxyl terminus.

23. The method of claim 22 wherein step (d) further comprises using the data identified in step (c) to:
(i) determine the limit of an intensity normalization process used with the liquid chromatography-mass spectrometry system and eliminate liquid chromatography-mass spectrometry data with variations beyond the limit;
(ii) determine whether variation in liquid chromatography-mass spectrometry system data of the liquid chromatography-mass spectrometry system is due to sample preparation or performance of the liquid-chromatography-mass spectrometry system;
(iii) to recalibrate mis-calibrated liquid chromatography-mass spectrometry data;
(iv) monitor the performance of a liquid chromatography column of the liquid chromatography-mass spectrometry system; or
(v) synchronize the retention times between a first liquid chromatography system and a second liquid chromatography system of the liquid chromatography-mass spectrometry system.

24. The method of claim 22, wherein each halogenated peptide standard independently comprises from about 2 to about 20 amino acids residues.

25. The method of claim 22, wherein each halogenated peptide standard independently comprises D amino acid residues.

26. The method of claim 22 wherein the sample is a biological sample.

27. The method of claim 26, wherein the biological sample is a body fluid, secreted proteins, cell surface proteins, plant-derived material, or a microorganism.

28. The method of claim 27, wherein the biological sample is human plasma.

* * * * *

SEQUENCE LISTING

```
<160> NUMBER OF SEQ ID NOS: 10

<210> SEQ ID NO 1
<211> LENGTH: 5
<212> TYPE: PRT
<213> ORGANISM: Artificial Sequence
<220> FEATURE:
<223> OTHER INFORMATION: Chemically synthesized; Halogenated peptide as
      standard for LC/MS
<220> FEATURE:
<221> NAME/KEY: MOD_RES
<222> LOCATION: (1)..(1)
<223> OTHER INFORMATION: Phe contains a bromo functional group
<220> FEATURE:
<221> NAME/KEY: MOD_RES
<222> LOCATION: (2)..(2)
<223> OTHER INFORMATION: Lysine is methlyated

<400> SEQUENCE: 1

Phe Lys Arg Tyr Gly
1               5

<210> SEQ ID NO 2
<211> LENGTH: 6
<212> TYPE: PRT
<213> ORGANISM: Artificial Sequence
<220> FEATURE:
<223> OTHER INFORMATION: Chemically synthesized; Halogenated peptide as
      standard for LC/MS
<220> FEATURE:
<221> NAME/KEY: MOD_RES
<222> LOCATION: (1)..(1)
<223> OTHER INFORMATION: Phe contains bromo functional group
```

```
<220> FEATURE:
<221> NAME/KEY: MOD_RES
<222> LOCATION: (2)..(2)
<223> OTHER INFORMATION: Lys is methylated

<400> SEQUENCE: 2

Phe Lys Gly Arg Tyr Tyr
1               5

<210> SEQ ID NO 3
<211> LENGTH: 7
<212> TYPE: PRT
<213> ORGANISM: Artificial Sequence
<220> FEATURE:
<223> OTHER INFORMATION: Chemically synthesized; Halogenated peptide as
      standard for LC/MS
<220> FEATURE:
<221> NAME/KEY: MOD_RES
<222> LOCATION: (1)..(1)
<223> OTHER INFORMATION: Phe contains bromo functional group
<220> FEATURE:
<221> NAME/KEY: MOD_RES
<222> LOCATION: (2)..(2)
<223> OTHER INFORMATION: Lys is methylated

<400> SEQUENCE: 3

Phe Lys Arg Tyr Gly Tyr Val
1               5

<210> SEQ ID NO 4
<211> LENGTH: 8
<212> TYPE: PRT
<213> ORGANISM: Artificial Sequence
<220> FEATURE:
<223> OTHER INFORMATION: Chemically synthesized; Halogenated peptide as
      standard for LC/MS
<220> FEATURE:
<221> NAME/KEY: MOD_RES
<222> LOCATION: (1)..(1)
<223> OTHER INFORMATION: Phe contains bromo functional group
<220> FEATURE:
<221> NAME/KEY: MOD_RES
<222> LOCATION: (2)..(2)
<223> OTHER INFORMATION: Lys is methylated

<400> SEQUENCE: 4

Phe Lys Gly Arg Tyr Tyr Val Tyr
1               5

<210> SEQ ID NO 5
<211> LENGTH: 6
<212> TYPE: PRT
<213> ORGANISM: Artificial Sequence
<220> FEATURE:
<223> OTHER INFORMATION: Chemically synthesized; Halogenated peptide as
      standard for LC/MS
<220> FEATURE:
<221> NAME/KEY: MOD_RES
<222> LOCATION: (2)..(4)
<223> OTHER INFORMATION: Each Phe contains p-chloro functional group

<400> SEQUENCE: 5

His Phe Phe Phe Ala Ala
1               5

<210> SEQ ID NO 6
<211> LENGTH: 4
<212> TYPE: PRT
<213> ORGANISM: Artificial Sequence
<220> FEATURE:
<223> OTHER INFORMATION: Chemically synthesized; Halogenated peptide as
```

```
      standard for LC/MS
<220> FEATURE:
<221> NAME/KEY: MOD_RES
<222> LOCATION: (1)..(2)
<223> OTHER INFORMATION: Each Phe contains a p-chloro functional group
<220> FEATURE:
<221> NAME/KEY: MOD_RES
<222> LOCATION: (4)..(4)
<223> OTHER INFORMATION: Lys contains C-terminal amine

<400> SEQUENCE: 6

Phe Phe Phe Lys
1

<210> SEQ ID NO 7
<211> LENGTH: 8
<212> TYPE: PRT
<213> ORGANISM: Artificial Sequence
<220> FEATURE:
<223> OTHER INFORMATION: Chemically synthesized; Halogenated peptide as
      standard for LC/MS
<220> FEATURE:
<221> NAME/KEY: MOD_RES
<222> LOCATION: (2)..(4)
<223> OTHER INFORMATION: Each Phe contains a p-chloro functional group
<220> FEATURE:
<221> NAME/KEY: MOD_RES
<222> LOCATION: (8)..(8)
<223> OTHER INFORMATION: Lys contains C-terminal amine

<400> SEQUENCE: 7

Ala Phe Phe Phe Ala Ala Ala Lys
1               5

<210> SEQ ID NO 8
<211> LENGTH: 8
<212> TYPE: PRT
<213> ORGANISM: Artificial Sequence
<220> FEATURE:
<223> OTHER INFORMATION: Chemically synthesized; Halogenated peptide as
      standard for LC/MS
<220> FEATURE:
<221> NAME/KEY: MOD_RES
<222> LOCATION: (3)..(5)
<223> OTHER INFORMATION: Each Phe contains p-chloro functional group
<220> FEATURE:
<221> NAME/KEY: MOD_RES
<222> LOCATION: (8)..(8)
<223> OTHER INFORMATION: Lys contains C-terminal amine

<400> SEQUENCE: 8

Ile Ile Phe Phe Phe Ala Ala Lys
1               5

<210> SEQ ID NO 9
<211> LENGTH: 12
<212> TYPE: PRT
<213> ORGANISM: Artificial Sequence
<220> FEATURE:
<223> OTHER INFORMATION: Chemically synthesized; Halogenated peptide as
      standard for LC/MS
<220> FEATURE:
<221> NAME/KEY: MOD_RES
<222> LOCATION: (3)..(5)
<223> OTHER INFORMATION: Each Phe has a p-chloro functional group
<220> FEATURE:
<221> NAME/KEY: MOD_RES
<222> LOCATION: (12)..(12)
<223> OTHER INFORMATION: Lys contains C-terminal amine

<400> SEQUENCE: 9

Ile Ile Phe Phe Phe Ile Ile Ala Ala Ala Ala Lys
```

```
<210> SEQ ID NO 10
<211> LENGTH: 13
<212> TYPE: PRT
<213> ORGANISM: Artificial Sequence
<220> FEATURE:
<223> OTHER INFORMATION: Chemically synthesized; Halogenated peptide as
      standard for LC/MS
<220> FEATURE:
<221> NAME/KEY: MOD_RES
<222> LOCATION: (4)..(6)
<223> OTHER INFORMATION: Each Phe contains p-chloro functional group
<220> FEATURE:
<221> NAME/KEY: MOD_RES
<222> LOCATION: (13)..(13)
<223> OTHER INFORMATION: Lys contains C-terminal amine

<400> SEQUENCE: 10

Ile Ile Ile Phe Phe Phe Ile Ile Ile Ala Ala Ala Lys
1               5                   10
```